(12) United States Patent
Shamay

(10) Patent No.: US 7,803,169 B2
(45) Date of Patent: Sep. 28, 2010

(54) BLOOD VESSEL OCCLUSION AUGER

(75) Inventor: Noam Shamay, Moshav Ptachia (IL)

(73) Assignee: Ovalum Ltd., Kiriyat Haim (IL)

( * ) Notice: Subject to any disclaimer, the term of this patent is extended or adjusted under 35 U.S.C. 154(b) by 570 days.

(21) Appl. No.: 11/602,106

(22) Filed: Nov. 20, 2006

(65) Prior Publication Data

US 2007/0083220 A1   Apr. 12, 2007

Related U.S. Application Data

(63) Continuation of application No. PCT/IL2005/000607, filed on Jun. 8, 2005.

(30) Foreign Application Priority Data

Jun. 9, 2004   (IL)   ..................... 162415

(51) Int. Cl.
*A61B 17/22* (2006.01)
(52) U.S. Cl. .............. 606/159; 606/7; 606/200
(58) Field of Classification Search ................. 606/159
See application file for complete search history.

(56) References Cited

U.S. PATENT DOCUMENTS

| | | | |
|---|---|---|---|
| 4,648,402 A | 3/1987 | Santos | |
| 4,848,342 A | 7/1989 | Kaltenbach | |
| 5,211,651 A | 5/1993 | Reger et al. | |
| 5,350,355 A | 9/1994 | Sklar | |
| 5,364,352 A | 11/1994 | Cimino et al. | |
| 5,554,163 A * | 9/1996 | Shturman | 606/159 |
| 5,632,758 A | 5/1997 | Sklar | |
| 5,653,722 A * | 8/1997 | Kieturakis | 606/159 |
| 5,662,606 A | 9/1997 | Cimino et al. | |
| 5,741,270 A | 4/1998 | Hansen et al. | |
| 5,842,984 A * | 12/1998 | Avitall | 600/374 |
| 5,954,742 A | 9/1999 | Osypka | |
| 6,113,615 A * | 9/2000 | Wulfman | 606/159 |
| 6,308,091 B1 * | 10/2001 | Avitall | 600/374 |
| 6,312,429 B1 | 11/2001 | Burbank et al. | |

(Continued)

FOREIGN PATENT DOCUMENTS

DE   3306213 A1 *   8/1984

(Continued)

OTHER PUBLICATIONS

Supplementary European Search Report dated Apr. 14, 2008 (5 pages), issued in counterpart European Application Serial No. 05747855.4.

(Continued)

*Primary Examiner*—Gary Jackson
*Assistant Examiner*—Julie A Szpira
(74) *Attorney, Agent, or Firm*—Frishauf, Holtz, Goodman & Chick, P.C.

(57) ABSTRACT

A blood occlusion auger having an in vivo distal auger tool coupled in operative association with an ex vivo auger control for opening and traversing occlusions in a blood vessel The auger control allows the selection of predetermined threshold forces and step-lengths values and operates in successive repetition of identical sequential stages, to traverse occlusions. Once disposed adjacent an occlusion, the auger tool, commanded by the auger control, operates in two states, first to radially dilate the vessel and second to penetrate distally into a furrow.

28 Claims, 16 Drawing Sheets

U.S. PATENT DOCUMENTS

| | | | |
|---|---|---|---|
| 6,440,147 B1 * | 8/2002 | Lee et al. | 606/159 |
| 6,579,302 B2 | 6/2003 | Duerig et al. | |
| 6,599,304 B1 | 7/2003 | Selmon et al. | |
| 6,620,179 B2 * | 9/2003 | Boock et al. | 606/159 |
| 6,638,247 B1 | 10/2003 | Selmon et al. | |
| 6,780,179 B2 * | 8/2004 | Lee et al. | 606/34 |
| 6,800,085 B2 | 10/2004 | Selmon et al. | |
| 7,303,531 B2 * | 12/2007 | Lee et al. | 600/564 |
| 7,399,307 B2 * | 7/2008 | Evans et al. | 606/194 |
| 2002/0123762 A1 * | 9/2002 | Lee et al. | 606/159 |
| 2008/0021449 A1 | 1/2008 | Burbank et al. | |

FOREIGN PATENT DOCUMENTS

| | | |
|---|---|---|
| EP | 117519 A1 * | 9/1984 |
| WO | WO 00/12009 A2 | 3/2000 |

OTHER PUBLICATIONS

Notification of Transmittal of the International Search Report and the Written Opinion of the International Searching Authority, or the Declaration for PCT/IL05/00607, dated May 23, 2007, 6 pages.

* cited by examiner

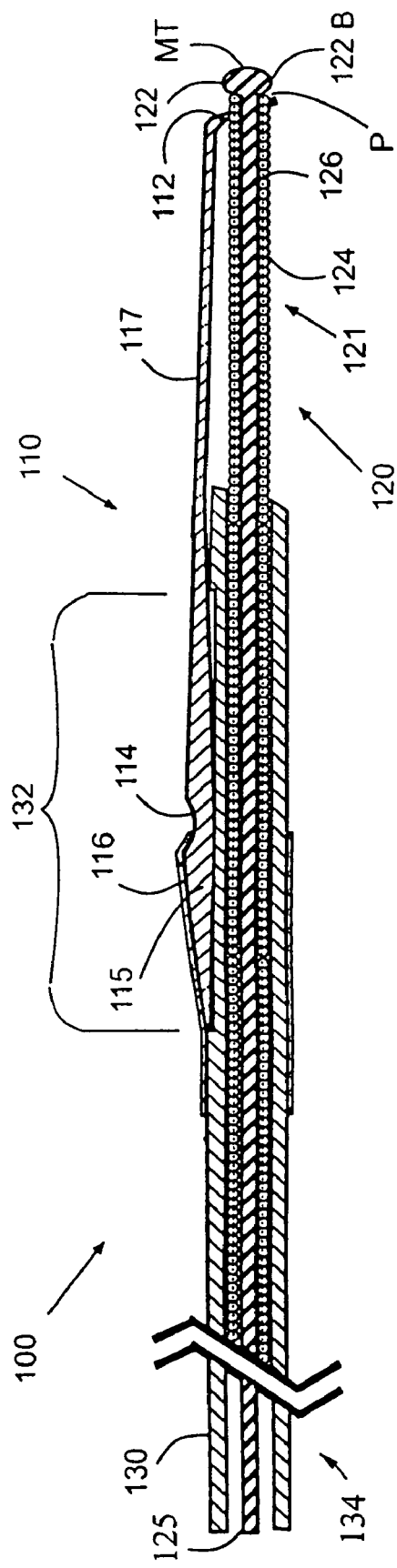
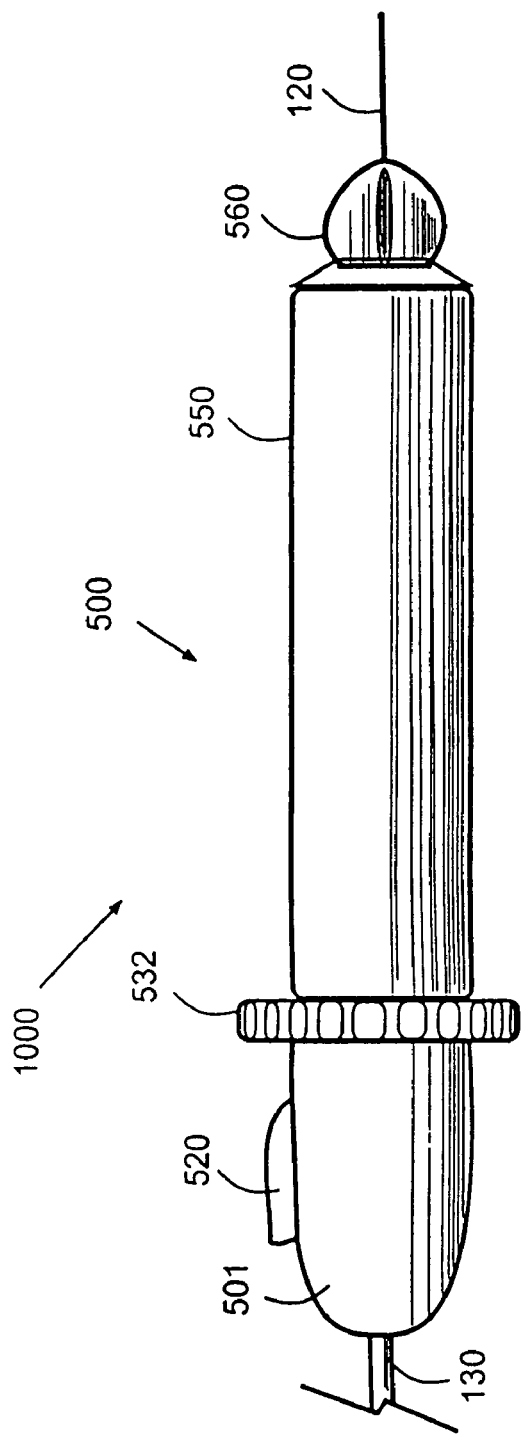
Fig. 3
Fig. 4

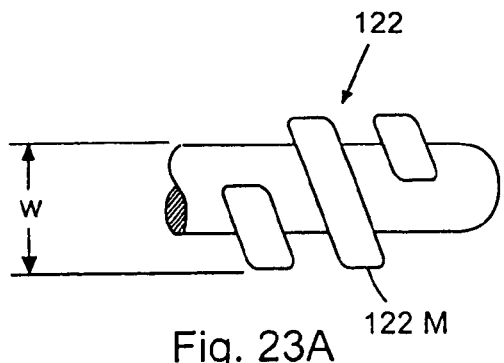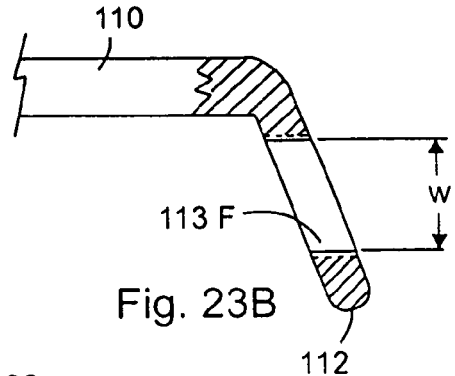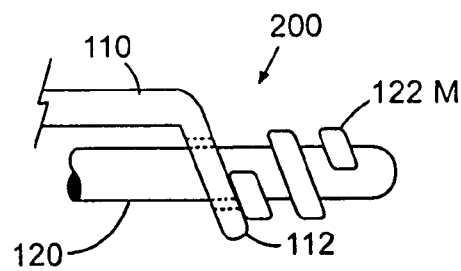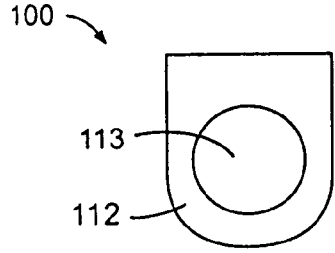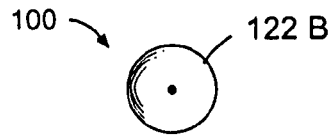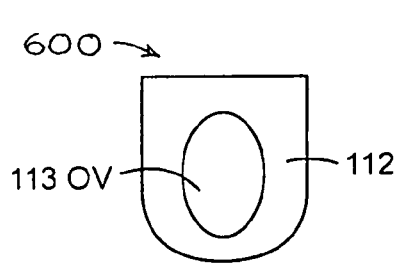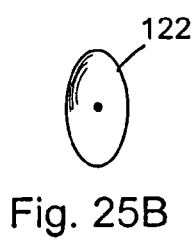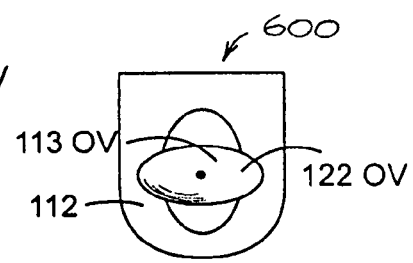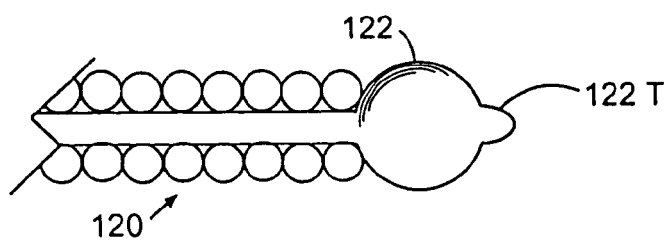

BLOOD VESSEL OCCLUSION AUGER

This application is a Continuation of PCT/IL2005/000607 filed Jun. 8, 2005, the priority date of which is claimed herein, and the entire disclosure of which is incorporated herein by reference.

Technical Field

The present invention relates to devices and methods for restoring blood flow in occluded blood vessels, and for traversing occlusions.

Definitions

Distal refers to both a direction of motion and a location, respectively, a movement in a direction away from an operator or a location further from the operator, for example a portion of an instrument located in vivo.

Proximal refers to both a direction of motion and a location, respectively, a movement in a direction toward the operator or a location nearer to the operator, for example a portion of an instrument located ex vivo.

Axial indicates the direction substantially in the longitudinal axis of a blood vessel.

Lateral and radial refer to a direction substantially perpendicular to the longitudinal axis of a blood vessel.

A furrow is considered hereinbelow as being a substantially axial furrow 340 in the vessel 300.

Background Art

Partial occlusion of any artery or vein of the body, herein a vessel, may slow blood flow to the extent that affected tissue may receive inadequate perfusion of life-giving oxygen, with sequelae of tissue ischemia, ischemic pain and tissue necrosis. In the heart, timely restoration of blood flow through occluded cardiac vessels can avert cardiovascular attack (CVA), tissue scarring, cardiac malfunction and/or death.

A preferred treatment for restoring blood flow through a partially occluded blood vessel uses a percutaneously-delivered wire having a spiraling wire jacket, herein a guide wire, whose leading end is positioned distal to the occlusion. In angioplasty, for example, the guide wire is used to guide a balloon to the occlusion site where the balloon is expanded, thereby radially dilating the occlusion, and increasing blood flow through the vessel.

In totally occluded blood vessels, including Chronic Total Occlusions (CTO's), the size of the occlusion and its hardness often make it impossible for a guide wire to navigate through and distally past the occlusion. Restoring blood flow through a totally occluded vessel often requires opening the chest and installing vessels that bypass the occlusion, a surgical procedure associated with high morbidity and risk of death.

Many tools exist for the treatment of occluded blood vessels, all having their drawbacks.

In U.S. Pat. No. 6,599,304, Selmon et al., teach a device with " . . . one or more hinged spreading or deflecting members that may be mechanically activated by an actuating member such as a pull wire or tube. A spreading or mechanical force may be thus applied to the blood vessel wall and occlusion so as to tear, fracture or otherwise disrupt, the occlusion adjoining the vessel wall. This disruption of the occlusion may create a channel or a passageway of sufficient size for the passage of a guidewire . . . ". The deflecting members are divulged as being jaws operated by an actuation element: "An actuation wire or actuation member 54 may be provided within the assembly to move the jaw sections 42 from its first closed position to its second open position. In various embodiments, the jaw sections 42 may have a variety of geometries, including but not limited to, spade shaped, straight with a concave curve at the end, straight with convex curve at the end, triangular (needle nose), rectangular and combinations thereof."

In U.S. Pat. No. 6,579,302, Duerig et al. teach a device with a spreader having a plurality of struts: "The spreader 15 may comprise a plurality of longitudinally or circumferentially arranged struts extending between the distal portion and the proximal portion of the spreader, such that advancing the spreader 15 over the core wire 20 frees the struts and allows them to expand to their largest diameter, and advancing the core wire 20 through the spreader 15 aligns the struts in a flat, closed position."

In U.S. Pat. No. 5,954,742, Osypka teach a device with an expander forming a cylindrical cage: "As can be seen, for example, in FIGS. 6, 7 and 8, the expander or dilator 5 forms an elongated at least substantially cylindrical cage surrounded by straight elongated sections 5a' of the expanding elements 5a, and the sections 5a' are at least substantially parallel to each other and to the central longitudinal axis of the cage."

In U.S. Pat. No. 5,741,270, Hansen et al., teach: "A pair of resilient connecting members 202 are mounted onto the bracing member mounting pins 208 and to the retracting member mounting pins 210. The connecting members 202 are made of thin strips of resilient material which regain their original shape after being deformed. One end of each of the connecting members 202 is pivotally connected onto the bracing member mounting pins 208, whereas the other end of each of the connecting members 202 is pivotally connected to the retracting member mounting pins 210."

In U.S. Pat. No. 4,648,402, Santos teaches a multilinkage mechanism: "Rear linkage 73 includes internal concave edge 773 and rear linkage 173 includes internal concave edge 873 which accommodate sphere 78 when it is in its most anterior position when mechanism 70 is in the closed configuration. In the open configuration of mechanism 70, there is also a net rearward displacement of front linkages 74 and 174, and of movable front section 76."

In U.S. Pat. No. 4,848,342, Kaltenbach teaches a rotatable dilation catheter with a spring coil: "The catheter includes a flexible wire or elongated member 1 which is provided with a swelling or head with a spherically curved surface 2 at its distal end. A spring coil 3 is slipped onto the wire 1 and this spring coil has opened turns which are radially expandable at its distal end to form a pressure member 4. In the illustrated embodiment, the coil 3 is a double coarse coil of steel wires, which adjacent a distal end of the wire 1 has an increased spacing between the adjacent turns to form open turns. The diameter of the pressure member can be increased by axially compressing the open turns of the spring coil 3."

In U.S. Pat. No. 6,800,085, Selmon et al., teach a catheter with a housing: "The distal mounted housing may further include one or more hinged spreading or deflecting members that may be mechanically activated by an actuating member such as a pull wire or tube." Furthermore, there is an actuation device: "An actuation member indicated by dotted lines 26 may move or actuate the blunt end member from a first closed position, as illustrated in FIG. 1, to a second open position, as illustrated in FIG. 2."

In U.S. Pat. No. 6,638,247, Selmon et al., teach a device with: "An actuation wire or actuation member 54 may be provided within the assembly to move the jaw sections 42 from its first closed position to its second open position. In various embodiments, the jaw sections 42 may have a variety of geometries, including but not limited to, spade shaped, straight with a concave curve at the end, straight with convex curve at the end, triangular (needle nose), rectangular and combinations thereof. The jaws 42 may be spaced apart or separated from one another even when closed as shown in FIG. 4."

None of the above mentioned disclosures teach an in vivo device having a bow, as a single asymmetric radially outward extensible flexible element with reduced radial dimensional configuration, and void of free radially extending extremities to prevent traumatic lesions to vessels, that dilates an occluded blood vessel and permits to traverse an occlusion in successively repetitively predetermined controlled identical steps. Additionally, controlled flexion and extension of the bow, in controlled force application and step-length, provide for a type self-propelled device that dilates an occluded blood vessel and permits to traverse an occlusion, without relying on the skills and dexterity of the operator.

DISCLOSURE OF THE INVENTION

An occlusion auger (100) is used for penetrating and traversing an occlusion (320) in a blood vessel (300) by performing a plurality of repeatable atraumatic single-sequence two-state consecutive actions including first radial dilatation in one direction to crack open a furrow (340) in the occlusion, followed second by distal penetration into the furrow, and vice versa.

An occlusion auger (100) having an ex vivo auger control operates an in vivo auger tool. Initially, the auger tool, trailing a shaft (130) containing a guide wire (120) is navigated adjacent the occlusion or in a furrow of the occlusion. In parallel or in sequence, predetermined values are set at the auger control, namely dilatation threshold forces and distal penetration step-length.

Next, the auger tool is operated under control of the predetermined values, to sequentially repeat identical radial dilation and distal penetration steps, without relying on the skills of the operator (OP). However, it is the task of the operator to conduct the auger tools axially into the vessel.

SUMMARY OF THE INVENTION

An aspect of some embodiments of the invention relates to a device for augmenting a blood flow passage through a partially or fully occluded blood vessel, the device including an auger tool adapted for use in an in vivo blood vessel. A vessel occlusion auger, or occlusion auger, having an auger tool commanded by an ex vivo auger control, is defined as a device for use in an invasive surgical procedure to open a lumen through a partial or total occlusion disposed in a blood vessel.

The auger tool is configured to provide atraumatic engagement of in vivo tissue, in rolling motion, under controlled force threshold and translation distance limits.

It is an object of the present invention to provide an occlusion auger (1000) and a method for implementing the occlusion auger, for distally traversing an occlusion (320) in a vessel (300) having vessel walls (310). There is provided an auger tool (110) configured for atraumatic repeatable operation in a sequence including both deflection to an arcuate state extending radially outward, and release to an expanded and straightened state, and vice versa. The auger tool has an extrados when arcuate, and also a tool tip (MT). In the arcuate state, when the auger tool is disposed adjacent the occlusion, the tool tip and the extrados are embedded and releasably retained in, respectively, a tip depression (141) and an arc depression (151) disposed opposite to each other in spaced-apart relationship in the vessel, whereby the vessel is dilated asymmetrically in radial outward direction for opening a furrow (340) in the occlusion.

Furthermore, in the expanded state, following the arcuate state, the tool tip translates into the furrow distally away from the arc depression, by one step length for each one sequence of operation. Each next sequence of operation of the auger tool is accompanied by a next distal tip depression, and a next distal arc depression, and both the next distal tip and the next arc depression are disposed distally relative to, respectively, a previous tip and a previous arc depression.

Moreover, the auger tool is configured for flexing in controlled deflection curve shape. Also, by embedding the tool tip first and thereafter the extrados induces atraumatic rolling motion is provided for radial outward dilation, and for distal translation.

It is another object of the present invention to provide an auger tool for operation in a specific number of successive sequences, accompanied by a same specific number of radial outward dilations and of distal translations. The auger tool translates substantially axially and distally into the vessel in successive crawling motion imparted by each successive sequence of operation.

It is yet another object of the present invention to provide an occlusion auger having a shaft (130) with an ex vivo proximal end (134), an in vivo distal end (135), an exterior (136), and an interior (137) supporting therein a wire (120) having an ex vivo proximal extremity (125) and an in vivo distal extremity portion (121). The auger tool (100) has a flexible and resilient bow (110) disposed in distal coextensive longitudinal alignment with the distal end of the shaft, and the bow has a bow back (117) intermediate a bow root (115) fixedly attached to and supported by the distal end of the shaft, and a face (112, 112T, 112OV) extending distally away from the bow back, the face having a face bore (113, 113F, 113OV), which is configured for passage therethrough of the wire. In addition, a force applicator (122, 122B, 122M, 122OV) retained at the distal extremity of the wire, is configured for operative association with the face bore and with the shaft, to flex the bow to the arcuate state when the shaft is translated distally relative to the force applicator, for the extrados to dilate the vessel in asymmetric radial outward direction, and to release the bow to the expanded state when the wire is released, for the face to translate the force applicator distally away relative to the arc depression by one predetermined step length for each one sequence of operation.

The force applicator has at least one flexible portion, and at least one resilient portion.

It is still another object of the present invention to provide a force applicator that is disposed in longitudinal coextensive distal alignment with the face, and where the bow is tangential to and longitudinally aligned with the shaft, and is configured to taper from the bow root distally away, forming a single protrusion extending radially outward relative to the wire, whereby alignment of the force applicator with the bow, tapering of the bow, and the single radial protrusion enhance reduced dimensions.

It is yet still another object of the present invention to provide a force applicator that is permanently attached to the distal extremity of the wire, and where the force applicator and the face bore are configured for either one of both, permitting passage of the force applicator through the face bore, and preventing passage of the force applicator through the face bore. In addition, the force applicator and the face bore may be configured for both, permitting passage of the force applicator through the face bore, and preventing passage of the force applicator through the face bore. Likewise, the force applicator may be retained to the face in proximally controlled attachment release.

It is a further object of the present invention to provide a bow that is configured with a distally gradually diminishing spring rate coefficient for deflection under larger force at the bow root and under smaller force at the face, whereby controlled atraumatic bow deflection curvature is achieved. Moreover, the bow is configured with a distally gradually diminishing spring rate coefficient for deflection under larger force at the bow root and under less force at the face, and the arc depression of the extrados is larger than the tip depression.

It is yet a further object of the present invention to provide occlusion auger having an auger control (500) that is disposed ex vivo in operative association with the auger tool, including a force limiter configured for adjustable selection and setting of a predetermined threshold limit of forces applied to the auger tool, and a step limiter configured for adjustable selection and setting of a predetermined distal step length taken in each one sequence of operation.

It is yet still a further object of the present invention to provide an auger control that maintains identical predetermined forces limit and step length settings for each sequence in a series of successively repeated sequences. Furthermore, the auger tool includes a shaft lock for releasably locking the shaft relative to the auger control and for limiting force applied on the shaft, and a stepper for distally translating the shaft in predetermined step length, a wire lock for releasably locking the wire relative to the auger control and for limiting force applied on the wire, and the auger control is configured for operative handling and control of the wire and of the shaft both independently and in combination.

It is an additional object of the present invention to provide an occlusion auger that when in the arcuate state has a bow back with an extrados extending radially outward and away from the wire, and the bow root is retained to the shaft, and the face is retained to the wire by the face bore, for continuous control of the deflection of the bow, whereby the force applicator is the sole free-extending extremity of the auger tool.

It is yet an additional object of the present invention to provide an occlusion tool that has at least one cutting edge (112C) disposed on a perimeter (112P) of the face to extend radially outward and away from the face bore, and where the at least one cutting edge is configured for radially cutting into occlusion tissue, in vivo It is yet still an additional object of the present invention to provide an occlusion tool where:

a. the force applicator is navigated to engage an axial furrow in an occlusion, b. the face is abutted on the force applicator, c. the auger tool is operated to the arcuate state, whereby kinetic energy is accumulated and the bow asymmetrically dilates the vessel into one radial outward direction, d. the auger tool is released to the expanded state, and the released kinetic energy extends the bow to translate the force applicator distally into the furrow, and e. the sequence of steps c. and d. are successively repeatable until the occlusion is traversed and augmented blood flow is restored.

It is one more additional object of the present invention to provide an occlusion tool where when in the arcuate state, the force applicator releasably embeds in a tip depression, the extrados embeds in an arc depression to dilate the furrow, and initiate a crack propagation mechanism to open and distally deepen the furrow, and when in the expanded state, the force applicator is received by one step length distally deeper in the deepened furrow.

It is yet still another additional object of the present invention to provide an occlusion tool where when in the arcuate state, the force applicator releasably embeds in a tip depression, the extrados embeds in an arc depression to dilate the furrow, and initiate a crack propagation mechanism to open and distally deepen the furrow, and when in the expanded state, the force applicator is received by one step length distally deeper in the deepened furrow It is still a further object of the present invention to provide an occlusion auger wherein when the force applicator extends distally past an occlusion, either one of both operations is performed:

the wire is navigated to engage a next occlusion and a next occlusion traversing sequence is performed, and the shaft is proximally retrieved ex vivo while the wire remains disposed in place for use in a next treatment intervention It is moreover a further object of the present invention to provide an occlusion auger wherein when the force applicator extends distally past a traversed occlusion, the shaft is retrievable ex vivo, by either one of both:

retrieving the face bore proximally away relative to the force applicator and sliding the face bore over the wire, and disengaging the face distally away from the force applicator, and retrieving the shaft proximally.

It is furthermore an object of the present invention to provide an occlusion auger wherein the auger tool is configured to accommodate locking, translation, and rotation of the shaft and of the wire in either one of both mutually independent operation, and in mutually associative operation.

It is furthermore still an object of the present invention to provide an occlusion auger wherein the arcuate state is achieved, by distal translation of the shaft relative to and over the wire until the face abuts the force applicator, and the expanded state is achieved by distal translation of the wire relative to the shaft. The distal translation has a step length that ranges from 1 mm to 50 mm.

It is yet still a further object of the present invention to provide an occlusion auger wherein the tip depression is disposed opposite the arc depression, and the arc depression has a span selected from the group of spans consisting of a span extending proximally and distally relative to the tip depression, a span extending proximally relative to the tip depression, and a span extending distally relative to the tip depression.

BRIEF DESCRIPTION OF THE DRAWINGS

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which:

FIG. 3 is a longitudinal cross-section of the side elevation shown in FIG. 2, FIG. 4 shows an ex vivo auger actuator for the operation of the vessel occlusion auger, FIGS. 23A to 23C depict a further embodiment of the auger tool, and FIGS. 24A, 24B, 25A to 25C, and 26 show details of various optional embodiments for the force applicator and the face of the bow,

BEST MODES FOR CARRYING OUT THE INVENTION

Figure 1:
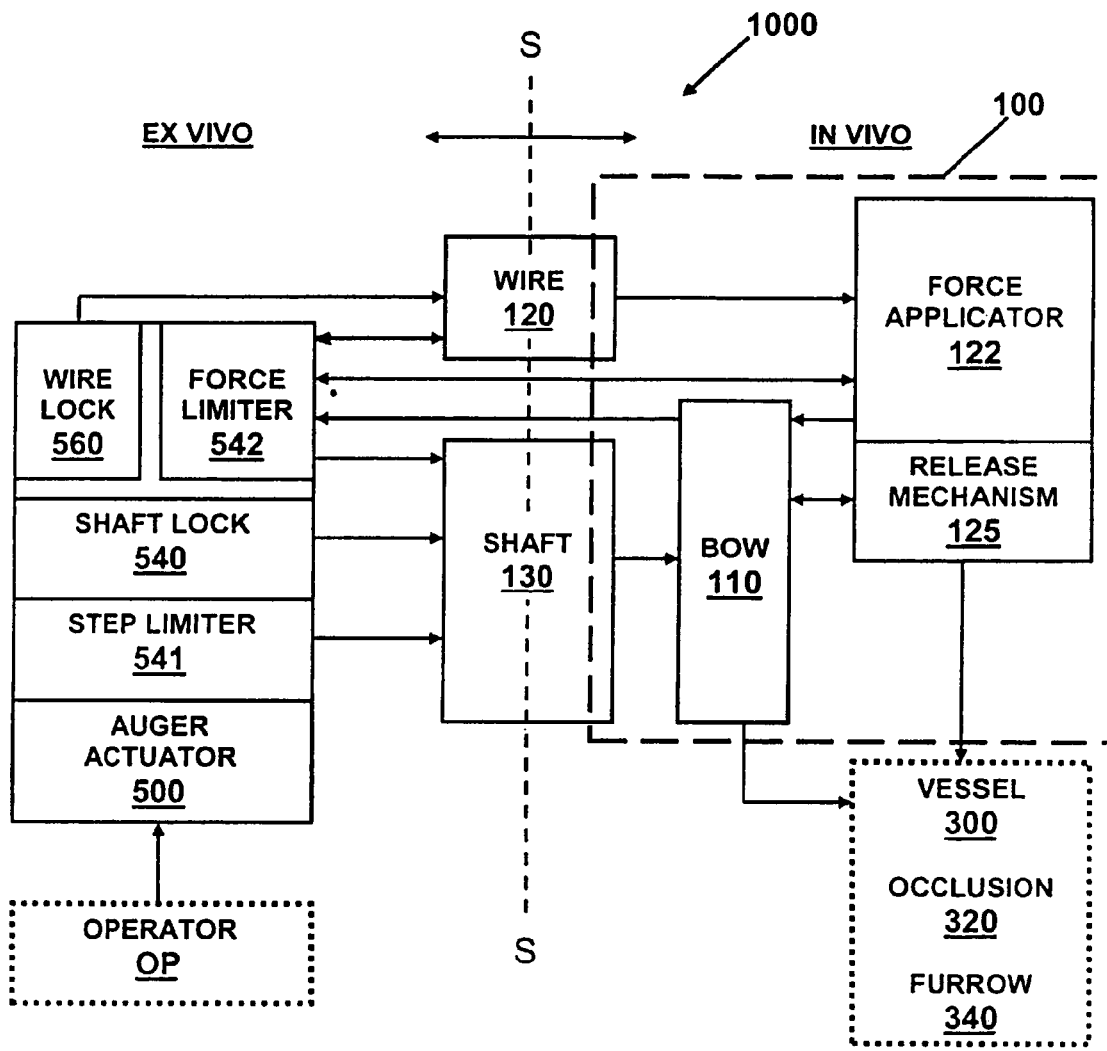
FIG. 1 is a schematic block diagram of the occlusion auger.

FIG. 1 presents a block diagram showing the mutual relationship and the main elements of the occlusion auger 1000 when in operation, with a proximal ex vivo portion, and a distal in vivo portion, shown separated by a dashed line S-S. A shaft 130 and a guide wire 120, or wire 120, both have a proximal ex vivo portion and a distal in vivo portion. A guiding catheter wherethrough the in vivo portion of the occlusion auger 1000 is introduced into the patient, and the patient, are not shown in FIG. 1.

An operator OP handles the occlusion auger 1000 via an ex vivo auger actuator 500, which controls an in vivo auger tool 100 operating a distal portion of the wire 120 and of the shaft 130. In the preferred embodiment 1000, the auger tool 100 has for example, a flexible and resilient element, such as a bow 110, fixedly coupled to the distal portion of the shaft 130, and removably engaging an in vivo force applicator 122 fixed to the in vivo distal extremity of the wire 120.

In operation, the wire 120 is first navigated distally via blood vessels 300, inside vessel walls 310, until the force applicator 122 engages an occlusion 320, or a furrow 340 in an occlusion 320. Then, the shaft 130 and the force applicator 122 are coupled and operated to flex and arcuate the bow 110. Thereby, the force applicator 122 and the extrados of the arcuate flexed bow back 117 are embedded in occlusion tissue lining the furrow 340, in releasable anchoring disposed adjacent opposite vessel walls 310.

In operation, flexing the bow 110 dilates the furrow 340 asymmetrically into one radial direction, providing forces to provoke and initiate a crack propagation mechanism in the occlusion 320, and to further open and distally deepen the furrow 340. Thereafter, forces on the bow 110 are released whereby the elastic energy accumulated therein while flexing is liberated to expand the bow 110, and to introduce the force applicator 122 by one step-length distally deeper into the furrow 340.

The flexure to arcuate and the release to expand the bow 110 are respectively, a first and a second state of a sequence having two phases, controllably operated in successive repetition by the auger actuator 500 to cross the occlusion 320. If necessary, repetitive operation of a plurality of sequences is reiterated successively to traverse one or more occlusions. Figuratively, the auger tool 100 coils-up when flexing, and uncoils when expanding, to progresses distally in a worm-like type of crawling process.

The auger actuator 500 has a shaft locking mechanism 540, or shaft lock 540, a step-length limiting mechanism 541, or stepper 541, and a force limiter 542, all coupled to the shaft 130. Furthermore, the auger actuator 500 has a wire locking mechanism 560, and a force limiter, other than the shaft force limiter, but also marked as 542 in FIG. 1, which are coupled to the wire 120. It is noted that the force applicator 122 and the bow 110 return feedback control information to the force limiter 542.

There is also an optional release mechanism 125 to decouple the force applicator 122 in vivo from the bow 120, as further described in detail hereinbelow.

Vessel Auger Assembly

Figure 2:
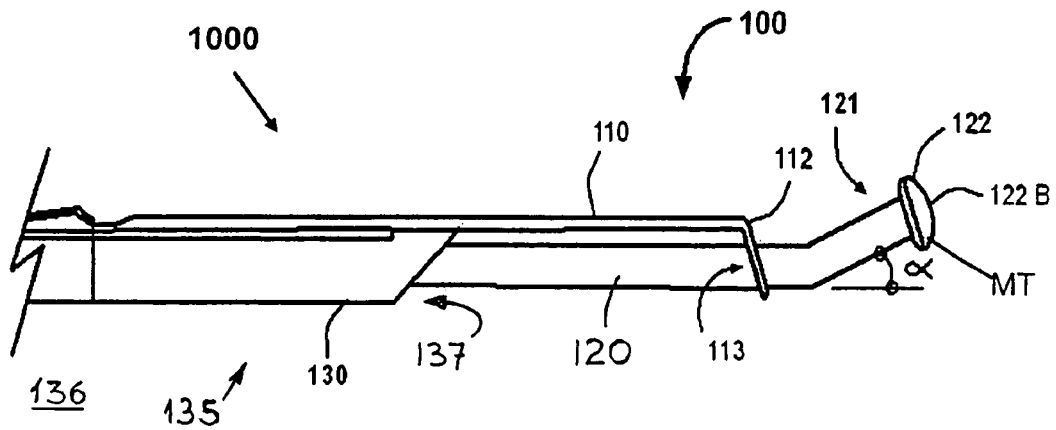
FIG. 2 shows a side elevation of the distal in vivo portion of the vessel occlusion auger, according to FIG. 1.

FIG. 2 shows a side elevation view of the in vivo auger tool 100, as an exemplary embodiment of a portion of the occlusion auger 1000, according to FIG. 1. The auger tool 100 includes a shaft 130, such as that of an available intravascular catheter system for the treatment of occluded blood vessels. The shaft 130 is distally terminated by, for example, a bow 110 that is flexible and resilient, and has a distal end terminated by a face 112 wherein a face bore 113 is opened. A guide wire 120, or wire 120, is disposed coaxially through the interior of the shaft 130 and through the face bore 113, which is configured to allow controlled bi-directional translation and rotation of the wire 120. The wire 120 has a flexible and resilient free distal extremity portion 121, terminated by a force applicator 122, shown as a bulb 122B, and accommodated to variably and reversibly extend distally away from the face 112. In an exemplary embodiment, both the force applicator 122 and the bow 110 include a radio opaque material so that an operator OP viewing an imaging system, for example a Computer Tomography (CT) or a Radiograph, may visualize the disposition of the force applicator 122 with respect to the face 112.

As shown in FIG. 2, the distal extremity portion 121 of the wire 120, extending distally away from the face 112, is bent to an angle a with respect to the shaft 130. When the wire 120 is rotated inside the shaft 130, then the distal extremity 121 becomes a directrix that describes the mantle of a cone. Therefore, when the wire 120 is disposed in the interior of a vessel 300, and the operator OP desires to introduce the distal extremity portion 121 past a curve or into a branch of a vessel 300, the wire 120 is rotated until the distal extremity portion 121 points into the direction appropriate to proceed past the curve or into the branch.

FIGS. 2 and 3 also indicate details of the shaft 130, such as the proximal end, the in vivo distal end, the exterior, and the interior, which supports a wire therein. Also shown are the ex vivo proximal extremity portion and the in vivo distal extremity portion, of the wire 120.

FIG. 3 is a longitudinal cross-section of FIG. 2, where the bulb 122B is shown retracted proximally and in abutment with the face 112, in contrast with the position depicted in FIG. 2, where the bulb 122B is shown in distal extension away from the face 112.

A relief 114, which locally decreases the cross-sectional area of the bow 110 defines a specific location about which the bow 110 will flex and bend when urged to arcuate. The shape of the relief 114 is irrelevant as long as the functional requirements are met, and may be implemented as a cutout formed by plane sections, or as a rounded-off curve of a selected shape. The shape of the relief 114 is thus not limited to any specific configuration and may be selected as desired.

The portion of the bow 110 extending from the proximal extremity thereof to the relief 114 forms a bow root 115, and the portion of the bow 110 extending from the relief 114 to the face 112 forms a bow back 117. The bow root 115 and a proximal portion of the bow back 117 are disposed in a cutout 132 entered in the distal portion of the shaft 130, so that the bow 110 longitudinally extends in co-alignment with the shaft 130. The bow 110 is made for example, from a super-flexible and resilient material, such as nitinol, and is exemplarily, about 1.4 centimeters long.

To reduce dimensions, the force applicator 122 is disposed in longitudinal coextensive distal alignment with the face 112, and the bow 110 is configured to taper from the bow root 115 distally away, to form a single protrusion extending radially outward relative to the wire 120. Thereby, due to the alignment of the force applicator 122 with the face 112, the tapering of the bow 110, and the single radial protrusion, reduced dimensions are enhanced.

Although not shown in the Figs., the bow 110 tapers distally away, thus having a larger cross-sectional area proximally than distally. Actually the bow 110 is one possible implementation of a portion of the auger tool 100. The bow 110 is a flexible and resilient beam cantilevered to the shaft 130 with the face 112 as the beam free end. The bow back 117 is actually a flat spring for which the distal taper provides a lower spring rate or spring coefficient at the distal extremity, here the face 112, than at the proximal cantilevered extremity, here the relief 114. The importance of the bow 110 being "softer" distally, and "harder" proximally is detailed hereinbelow.

In an exemplary embodiment, the bow root 115 and at least a proximal portion of the relief 114, are belted by a surrounding shrink tube 116. The shrink tube 116 is shrunk to fixedly retain the bow 110 in co-alignment to the shaft 130, and to prevent any relative motion between the bow 110 and the shaft 130. The shrink tube 116 also grips the relief 114 to better anchor the bow 110 onto the shaft 130. The bow back 117 is not covered by the shrink tube 116, and is thus free to flex.

The fixed retention of the bow root 115 to the shaft 130 is possibly achieved with any practical means available, and is not restricted to the use of a shrink tube 116, as further described hereinbelow. If desired, the shrink tube 116 is selected from materials that can be induced to form a strong attachment to the bow 110, for example, materials including Nylon 11™ or Nylon 6™. It is remarked that the shaft 130 may have a diameter of 0.55 mm for example.

FIG. 3 illustrates a coiled spiraling wire jacket 124 encasing the distal extremity portion 121 of the wire 120. The wire jacket 124 is about 20 cm long and remains conformal to the wire 120 that tapers distally along that same length, from, say a diameter of 0.05 mm, down to 0.01 mm. In an exemplary embodiment, the face bore 113 has a diameter of 0.3 mm and the bulb 112B is 0.35 mm in diameter.

FIG. 3 also depicts that the distal portion of the wire 120 includes a core wire 126 encased in the spiraling wire jacket 124. In an exemplary embodiment, the wire jacket 124 is 1 to 0.5 millimeters in diameter and the core wire 126 has a diameter ranging from 0.05 mm to 0.01 mm. For the sake of clarity, reference is made hereinbelow simply to "wire 120".

Although the auger tool 100 was described as having a bow 110, other implementations are possible, as long as the functional and atraumatic requirements are respected. This means that it is always necessary to assure controlled tension and flexure forces, to control radial outward extension in the arcuate state, as well as distal translation when in return to the expanded state.

Figure 5:
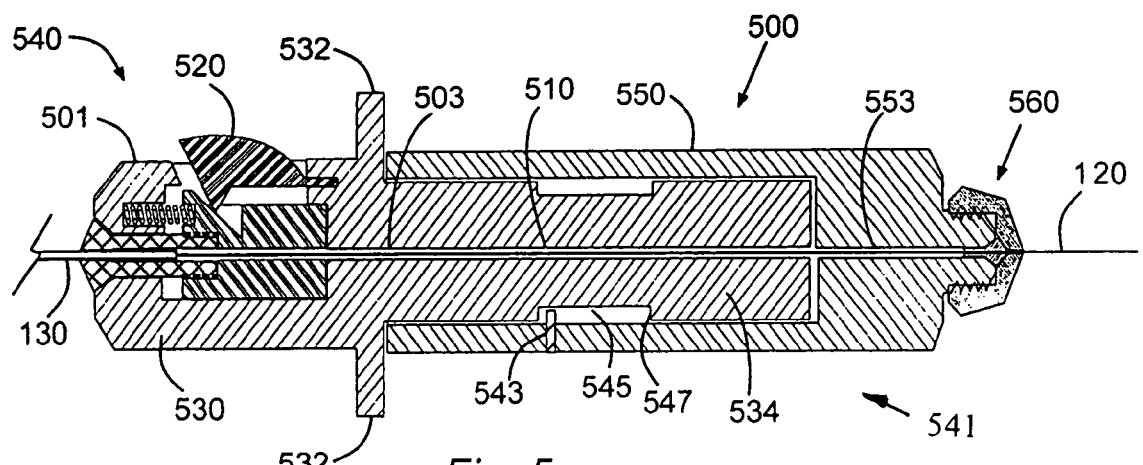
FIG. 5 is a longitudinal cross-section of the auger actuator shown in FIG. 4.

FIG. 4 presents the ex vivo auger actuator 500 for the operation of the in vivo auger tool 100, and FIG. 5 is a longitudinal cross-section of FIG. 4.

Referring to FIGS. 4 and 5, the auger actuator 500 includes a distal shaft control 501 supported concentrically in proximal co-aligned extension by a substantially cylindrical wire handle 550. A common axial conduit 510 pierces both the distal shaft control 501 and the wire handle 550. A distal portion 503 of the conduit 510 passing throughout the distal shaft control 501 is configured to accommodate free passage therethrough of the shaft 130, whereas a proximal portion 553 of conduit 510 passing throughout the wire handle 550 is configured to accommodate free passage therethrough of the wire 120. The shaft 130, which is disposed in the wider portion 503, cannot penetrate into the narrower proximal portion 553 of the conduit 510 passing through the wire handle 550.

The shaft control 501 is of unitary construction and includes a shaft-nose 530, a collar 532, and a shaft body 534, all of generally cylindrical shape and disposed in concentric coextensive alignment. The shaft-nose 530 is oriented in the distal direction, proximally followed first by the collar 532 and second, by the shaft body 534. The collar 532 protrudes radially outward and away from the external surface of the shaft-nose 530, the shaft body 534, and the wire handle 550. A wire locking mechanism 560, or wire lock 560, is proximally and coaxially appended to the wire handle 550.

FIG. 5 further depicts a step limiter 541, or stepper 541, for setting a step length, for example by help of a setscrew 543 coupled to the wire handle 550, where the setscrew 543 is received in a relief 545 cut in the shaft body 534, operating as described hereinbelow.

The shaft body 534 is configured as a male cylinder coaxially received in the interior of an axial female bore entered into the wire handle 550, and is configured to permit mutual relative displacement in bi-directional translation and in bi-directional rotation, between both the shaft control 501 and the wire handle 550. Relative to the wire handle 550, the collar 532 is displaceable in bi-directional rotation and in translation distally outward and away therefrom, and proximally back therein. The auger actuator assembly 500 is designed to permit precise control of the bi-directional displacement in translation and in rotation of both the wire 120 and of the shaft 130, as described in detail hereinbelow.

Figure 6:
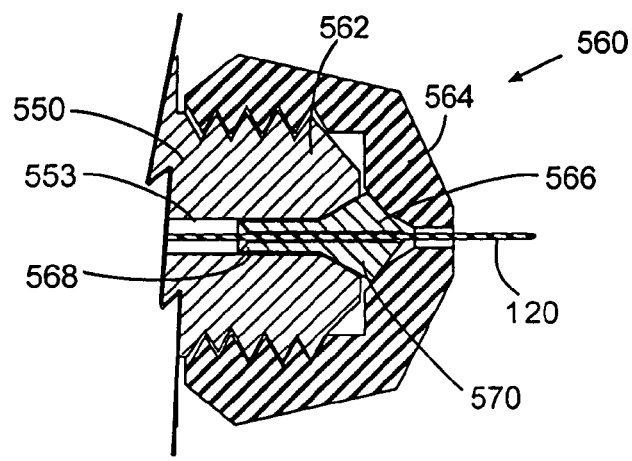
FIG. 6 is an enlarged detail of the wire-locking mechanism of the auger actuator shown in FIG. 5.

FIG. 6 is an enlarged detail of the wire-locking mechanism 560, having a configuration well known to the art, and permitting to reversibly lock the guide wire 120 relative to the wire handle 550, when desired. A threaded extension 562 carrying an external male screwthread is disposed concentrically and in proximal coextension to the proximal extremity of the wire handle 550 for matching engagement with a female screwthread disposed on the interior of a cap nut 564. The proximal portion 553 of the common axial conduit 510 coaxially pierces both the threaded extension 562 and the cap nut 564.

A wire glans 566, having an axial bore for the passage of the wire 120 therethrough, has a wire stem 568 and wire locking jaws 570. The wire stem 568 and the wire locking jaws 570 are received in an appropriate widening entered in the proximal extremity 553 of the axial conduit 510. The wire locking jaws 570 of the glans 566 resiliently separate into a plurality of flexible and resilient jaws configured to operate as a cone-locking mechanism. Further details for this well-known cone-locking mechanism are superfluous.

It is understood that when the female cap nut 564 is threadingly engaged on the male screw-threaded tail 562, the cap nut 564 applies compression forces on the wire locking jaws 570 that deflect to firmly lock onto the wire 120 and prevent displacement thereof relative to the wire handle 550. It is also clear that when the female cap nut 564 is threadingly disengaged from the male threaded tail 562, the wire locking jaws 570 resiliently release their grip on the wire 120, which then becomes able to freely translate and rotate relative to the wire handle 550.

When the wire locking mechanism 560 is locked onto the wire 120, and the wire handle 550 is rotated clockwise and anticlockwise, then the wire 120 will rotate in the same direction, respectively, clockwise and anticlockwise. Likewise, the wire 120 can now be translated longitudinally distally or proximally to, respectively, extend distally out, as shown in FIG. 2, or to retract proximally.

In an exemplary embodiment, the wire locking jaws 570 are made from a material including for example, metal, such as brass, or a polymeric plastic material known by the trade name Acculon™.

The wire locking mechanism 560 has a built-in force limiting mechanism. The force applied by the wire locking jaws 570 on the wire 120 define the load under which the wire will slip out of the wire locking jaws 570. Thus the more and the harder the cap nut 564 is screw threaded on the male threaded tail 562, the higher the retention force on the wire 120, and vice versa. Other force limiting mechanisms are also applicable. Indication of the retaining force threshold of the wire 120 may also be provided.

As described hereinbelow, translation, rotation, and standstill of the wire 120 and of the shaft 130 are mutually independent, but may be operated in cooperative association.

Figure 7:
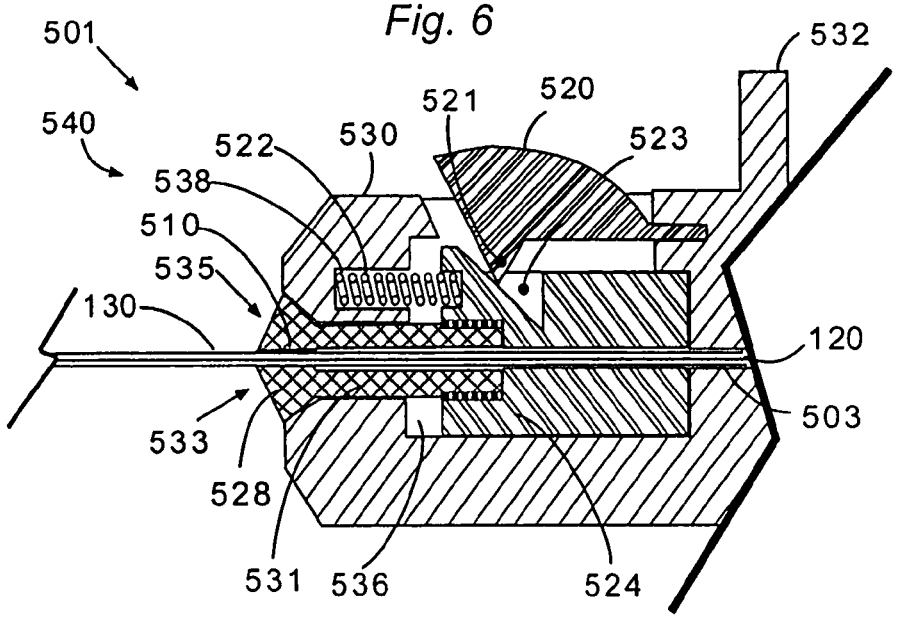
FIG. 7 is an enlarged detail of the shaft locking mechanism of the auger actuator shown FIG. 5.

FIG. 7 shows a longitudinal axial cross-section of a shaft locking mechanism 540 disposed in the distal portion of the shaft control 501 in which a plurality of shaft locking jaws 528 releasably lock onto the shaft 130, thereby preventing longitudinal and rotational displacement of the shaft 130 relative to the shaft control 501.

In an exemplary embodiment, the shaft nose 530 is accommodated with a concentric nose opening 535 for receiving therein a shaft stem 531 of a shaft glans 533 having a plurality of flexible and resilient shaft locking jaws 528. The shaft locking jaws 528, concentrically pierced by the distal portion 503 of the axial conduit 510, operate to releasably lock onto the shaft 130 by a cone-locking mechanism configuration well known to the art.

The shaft glans 533 is fixedly coupled in axial co-aligned disposition to a slider 524 accommodated to freely translate axially and longitudinally, thus both distally and proximally, in the interior of a chamber 536. The chamber 536 is a hollowed out volume disposed in the interior of the shaft nose 530. A resilient element 522, such as one or more helical coil spring(s) 522, appropriately housed in a blind spring bore 538 opened in parallel to the conduit 510 into the shaft nose 530, are accommodated to receive the spring(s) 522. The resilient element 522 biases the slider 524 proximally away. Thereby, the slider 524 retracts the shaft glans 533 into the shaft nose 530, whereby the shaft locking jaws 528 lock onto the shaft 130, preventing translation and rotation thereof relative to the shaft control 501.

When the shaft locking mechanism 540 is locked onto the shaft 130, and the collar 532 is translated distally and proximately, or rotated, then the shaft 130 also, respectively, translates distally and proximately, or rotates, relative to the wire handle 550, shown in FIG. 5.

To release the locked shaft 130, the slider 524 is translated distally, whereby the shaft locking jaws 528 are pushed distally out of the nose opening 535, and flex radially out and away. Thereby, the resilient shaft locking jaws 528 open to release grip and release the shaft 130 to freely translate and rotate. To this end, a plunger 520, retained in pivotal freedom of motion to the shaft control 501, is provided with a wedge 521 configured to engage a matching groove 523 accommodated for this purpose in the slider 524. When the operator OP depresses the plunger 520, then the wedge 521 pivots to engage the groove 523. Thereby the slider 524 is driven distally against the resilient element 522, to release the lock of the resilient shaft locking jaws 528 on the shaft 130.

When the shaft-locking mechanism 540 is released by depression of the plunger 520, the shaft 130 is free to translate and rotate. It is also understood that the purpose of translation and rotation of the guide wire 120 and of the shaft 130 is to allow an operator OP to precisely operate and position the auger tool 100 with respect to an occlusion 320 disposed in a vessel 300. Moreover, the plunger 520 operates as an emergency button, permitting to immediately disconnect the shaft and to relieve the vessel 300 from any force or moment applied thereon by the auger tool 100.

The shaft-locking mechanism 540 has a built-in force limiting mechanism, permitting to select a threshold limit to prevent the exertion of excessive forces on the force applicator 122, and on the bow 110. The bias exerted by the resilient element 522 on the slider 524 is the force by which the shaft glans 533 is pulled proximally, and the more spring bias, the more forceful the proximal pull. The proximal pull of the slider 524 is applied to the shaft glans 533 to lock the shaft 130 with a force proportional to the bias applied by the resilient element 522. One shaft retaining force control mechanism consists of replacing an installed resilient element 522 by a harder or softer one, to obtain, respectively, higher or lower shaft retention locking forces.

Other shaft-locking force control mechanisms are possible. One example, not shown in the Figs., is the preloading of a spring 522, say by operating a controllable screw for the releasable axial compression of the spring. The more the spring 522 is compressed, the better the shaft locking jaws 528 clamp the shaft and the higher the lock retention forces on the shaft 130.

Hence, when the bow 110 is flexed to arcuate, a force of magnitude lower than a limit threshold will prevent breakage of the guide wire 120 and separation of the force applicator 122 therefrom. In addition, the radial force of the bow 110 against a vessel wall 310 may be kept below a threshold limit, to prevent damage to a vessel 300.

In an exemplary embodiment, the shaft locking jaws 528 are made from an elastomeric material including, for example, a polymeric plastic material known by the trade name Teflon™. Given the relatively low coefficient of friction of the selected material, the shaft-locking mechanism 540 will give way above a determined force, to allow the shaft 130 to slip on the shaft locking jaws 528, and prevent the application of a higher than desired force on the wire 120, on the force applicator 122, and on the bow 110.

FIG. 5 depicts a conceptual embodiment of the step-length limiter 541, also indicated in FIG. 1. The setscrew 543, coupled to the wire handle 550, and extending radially inward to be received in the relief 545, operates as a stopper to limit the step-length. When the shaft body 534 is translated distally, the translation will stop when the setscrew 543 abuts the proximal wall 547 of the relief 545. Assuming that the shaft lock 540 is locked on the shaft 130, and the wire lock 560 is locked on the wire 120, then when the shaft body 534 is translated distally, stopping of the translation of the setscrew 543 on the proximal wall 547 will limit the distal translation step-length imparted to the shaft 130 relative to the wire 120.

The step-length limiter 541 is possibly implemented in various versions, not described herein. For example, the setscrew 543, or any other mechanical stopper such as a pin, may be disposed in adjustable setting on the wire handle 550 relative to the proximal wall 547, to provide for an adjustable step-length. Although not shown in the Figs., one may also consider piercing bores into the wire handle 550, at various distances from the proximal wall 547, to achieves various step lengths when the setscrew 543, or a pin, are entered into an appropriately selected bore. Evidently, other implementations of the step-length limiter 541 are possible.

The operator OP is thus presented with a multi functional auger control 500, having a shaft lock 540 for releasably locking the shaft 130 relative to the auger control 500 and for limiting force applied on the shaft 130, a stepper 541 for distally translating the shaft 130 in predetermined step length, a wire lock 560 for locking the wire 120 relative to the auger control 500 and for limiting force applied on the wire. It is noted that the auger control 500 is configured for operative handling and control of the wire 120 and of the shaft 130 both independently and in combination. In addition, it is noted that the shaft 130 may be retrieved distally out of the auger control 500, and that the wire 120 may be retrieved out of the auger control 500 both distally and proximally.

The auger control 500 is thus disposed ex vivo in operative association with the auger tool 100, including an inherent force limiting mechanism configured for the adjustable selection and for the setting of a predetermined threshold limit of shaft forces and of wire forces applied to the auger tool 100, and a step limiter configured for the adjustable selection and for setting of a predetermined distal step length identically taken and repeated in each one sequence of operation. It is not the operator OP but the auger control that maintains identical predetermined forces limit and step length settings for each sequence in a series of successively repeated sequences.

Treating an Occluded Vessel

Figure 8:
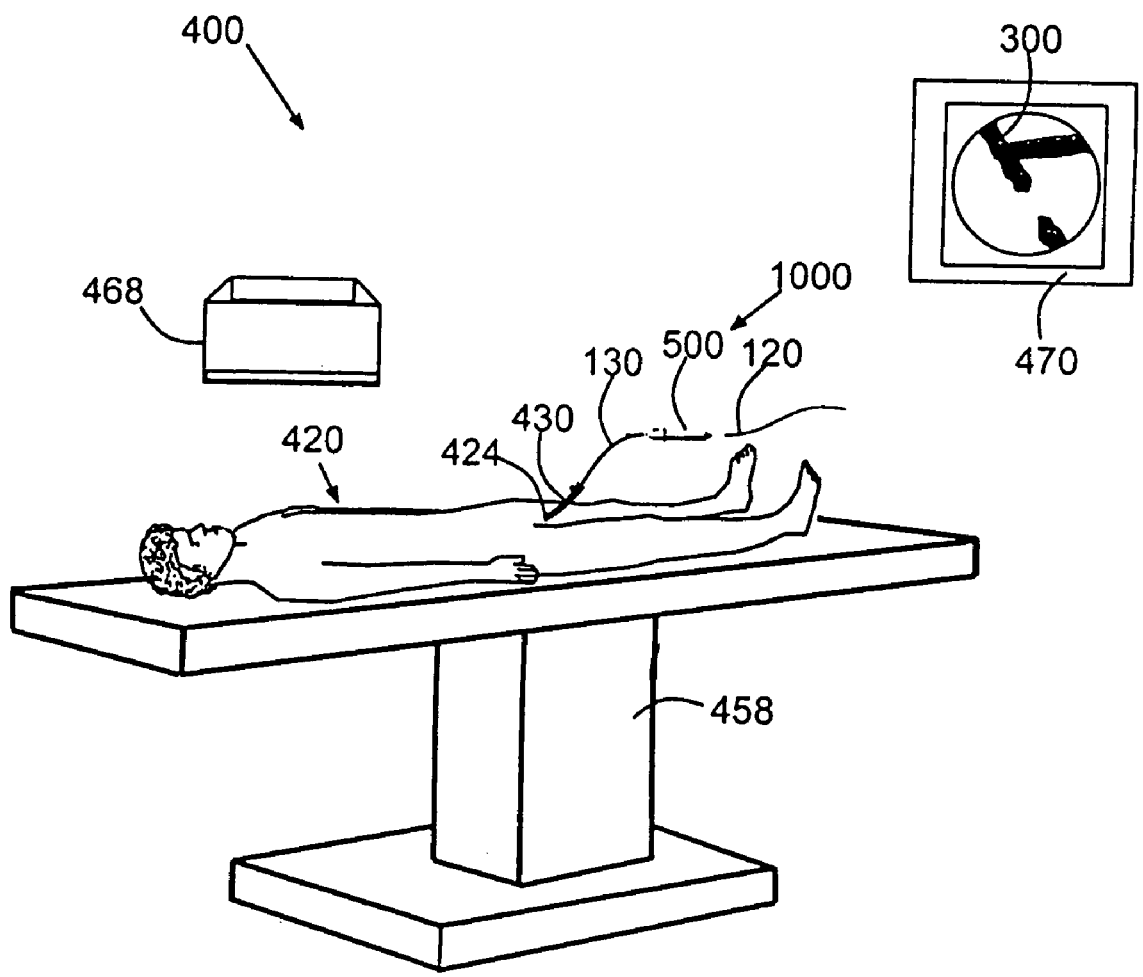
FIG. 8 shows a typical operating room used for a procedure with the occlusion auger according to FIG. 1, FIGS. 9 and 10 show partial in vivo cross-sections of a procedure with the occlusion auger according to FIG. 1, FIGS. 11A, 11B, 12A to 12C, 13A, 13B, and 14A to 14C show details of the navigation and the use of the occlusion auger of FIG. 1, FIGS. 15A, 15B, 16A, 16B, 17A, 17B, and 18, show details of the operation of the occlusion auger of FIG. 1.

FIG. 8 shows a typical operating room 400 used for a procedure with the occlusion auger 1000 that includes a surgical table 458, an imager 468 and an imaging display 470 that provides a real-time image of a treated vessel 300. In an exemplary embodiment, wherein the coronary artery 300 is being treated, a patient 420 is placed in the prone position on the table 458 and the shaft 130 is passed through a catheter 430 that enters the patient 420 through an incision 424 into a femoral artery 428, as illustrated in FIG. 9.

Figures 9, 10:
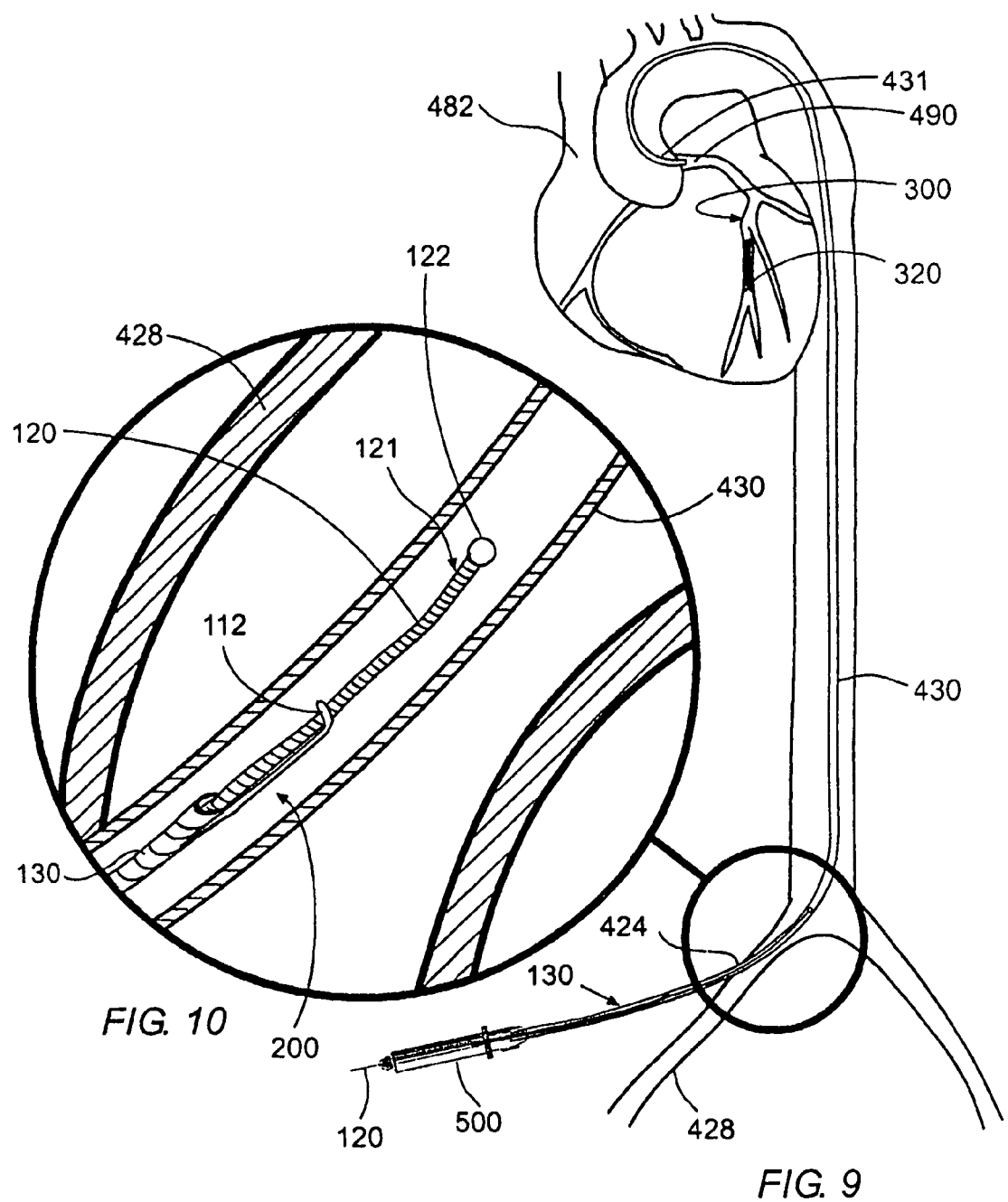

FIG. 9 and FIG. 10, which is an enlarged detail of FIG. 9, show a partial in vivo cross-section of the guiding catheter 430 entering through an incision 424 into the femoral artery 428, seen in cutaway. The auger actuator assembly 500 is manipulated so that the shaft 130 passes through the guiding catheter 430 toward a heart 482, where a catheter distal end 431 communicates with a coronary artery 490 having a vessel branch 300 that contains an occlusion 320.

To treat an occlusion 320, it is first necessary to navigate the distal portion of the occlusion auger 1000 via vessels 300 until the auger tool 100 meets the occlusion 320. The auger tool 100 is operated with the force applicator 122 being extended distally away from the face 112, as seen in vivo in FIG. 10. The distal wire extremity portion 121, terminated by the tool tip MT, hangs free in a flexible configuration, allowing the wire 120 to flex and curve through bends and branches encountered in blood vessels.

In practice, the occlusion auger 1000 is supplied with a wire 120 that is about 185 cm long, and a shaft 130 having a length of some 140 cm. By factory setting, the force applicator 122 extends some 45 cm distally away from the face 112. That distance generally suits the operator. Extension pieces, not shown in the Figs. but used in common practice, may be attached to both the wire 120 and the shaft 130, if desired.

It is always possible to alter this factory-set disposition. To extend the bulb 122 distally away from the face 112, the auger occlusion assembly 500 has to be manipulated as follows. The shaft locking mechanism 540 is locked while the wire locking mechanism 560 is released and the guide. wire 120 is manually pushed distally relative to the wire handle 550, to extend say for some 40 to 100 mm. To maintain a selected distance between the force applicator 122 and the face 112, the wire locking mechanism 560 is locked, as is the shaft locking mechanism 540, so that translation of the auger tool 500 will simultaneously translate both the wire 120 and the shaft 130.

Figure 11:
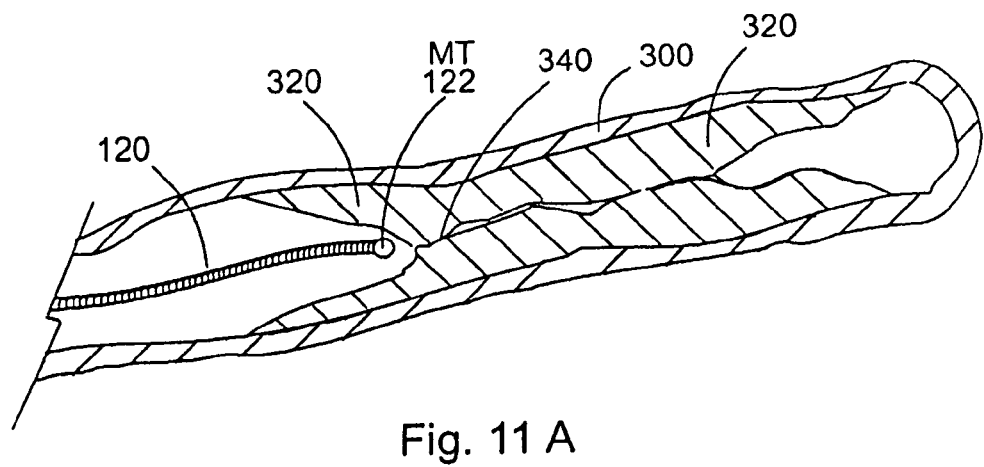
Figure 11:
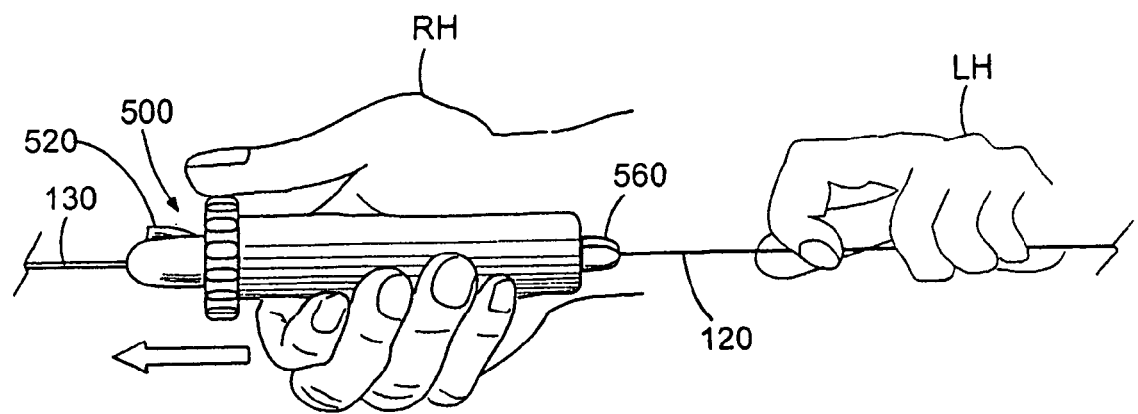

In a first step, as shown in vivo in FIG. 11A, the operator navigates simultaneously both the shaft 130, not shown in FIG. 11A, and the wire 120, or only the wire 120, distally into the vessel 300, in manual translation toward and until the tool tip MT, here the force applicator 122, contacts the occlusion 320 as distally as possible, into the furrow 340.

In a second step, the shaft locking mechanism 540 is locked, and the wire locking mechanism 560 is unlocked. The guide wire 120 is kept in place by being firmly retained in one hand by the operator OP, say in the left hand LH, while the other hand pushes the auger actuator 500, thus also the shaft 130, in distal translation over the wire 120, as shown ex vivo in FIG. 11B. It is noted that the shaft locking mechanism 540 is locked since the plunger 520 is not depressed. The distal translation terminates when the face 112 comes to rest in abutment with the force applicator 122, as shown in vivo in FIG. 12A.

It is noted that when the face 112 abuts the force applicator 122, the bow 110 increases the rigidity of the distal extremity portion 121 of the guide wire 120, which is thereby stiffened. In addition, a visual feedback signal is provided ex vivo to the operator OP, to indicate that the bulb 122 is in mechanical contact with the face 112, by uncovering a mark, not shown in the Figs., disposed on the wire 120. A mark, sign, or indicia, is appropriately disposed on a proximal portion of the wire 120, so that when the shaft is introduced distally to have the face 112 abut the bulb 122, the mark is uncovered ex vivo when contact is made, by appearing proximally out of the auger actuator assembly 500.

By use of common practice radio opaque material, the disposition and the relative location of the various components of the auger tool 100 are also presented to the operator on an X-ray device.

To orient the face 112 in an appropriately selected direction for further engagement as deep as possible into the furrow 340 of an occlusion 320, the shaft locking mechanism 540 and the wire locking mechanism 560 are first locked. Next, the auger actuator 500 is held by hand, as shown ex vivo in FIG. 12B, and the collar 532 is rotated in the desired direction, say by the thumb T, to rotate the shaft 130 together with the bow 110 and the face 112. With both the wire locking mechanism 560 and the shaft lock mechanism 540 locked, it is possible to rotate the collar 532 in either direction and to translate the shaft 130 distally, as shown ex vivo in FIG. 12B by, respectively, the arrows A and R.

Evidently, it is also possible to unlock the wire locking mechanism 560, to extend the force applicator 122 distally away from the face 112, and to handle the guide wire 120 independently, even though the former configuration is more rigid than the latter.

Figure 12:
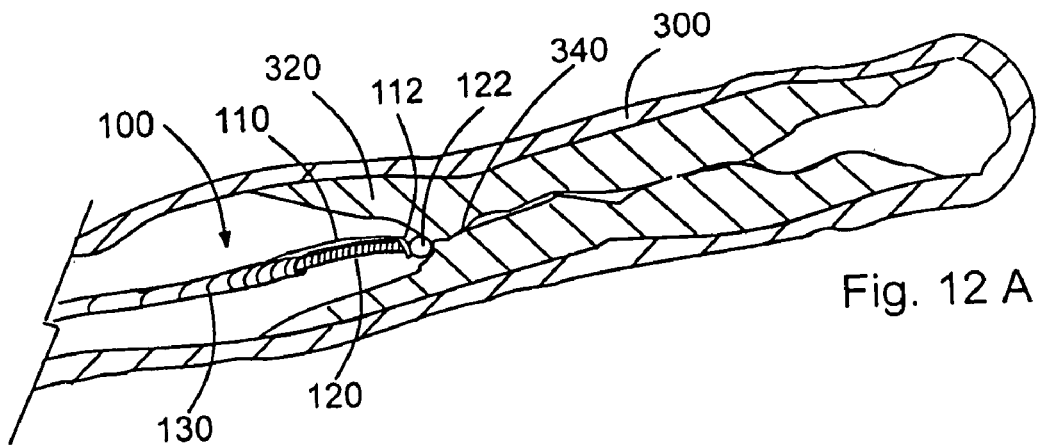
Figure 12:
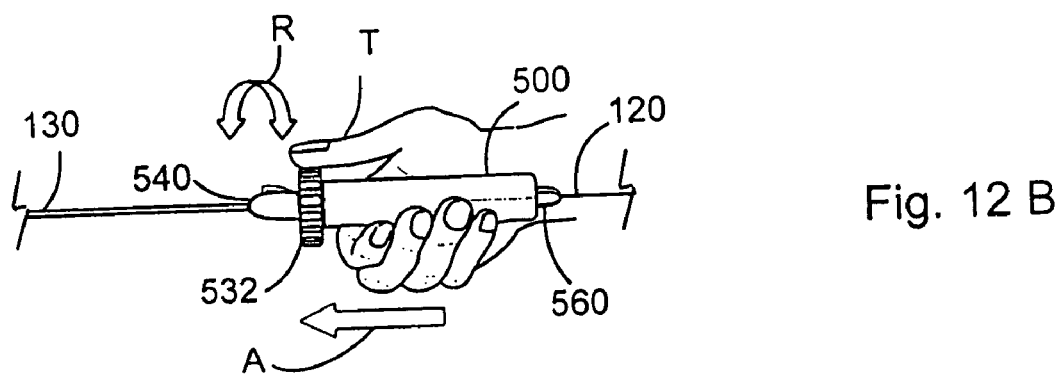
Figure 12:
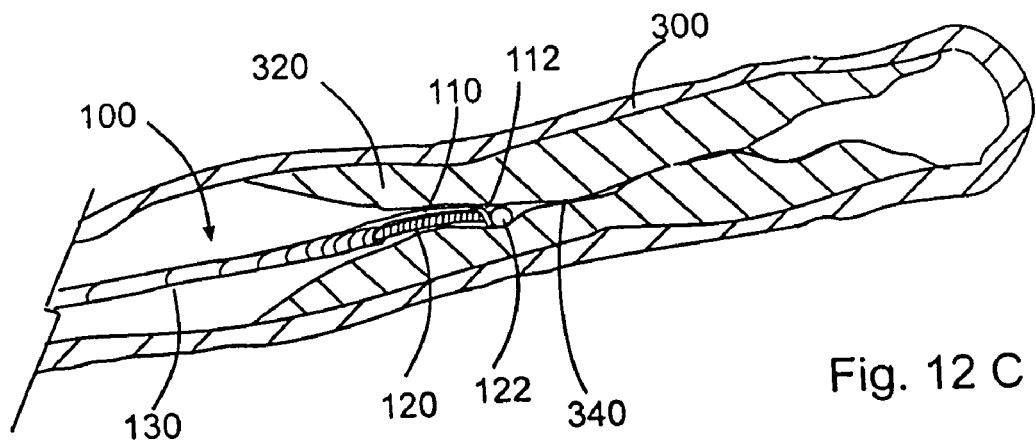

The auger tool 100 is now well positioned to threat an occlusion 320, either if penetration of the force applicator 122 into the furrow 340 was successful, as by FIG. 12C, or even when the force applicator 122 only abuts on the occlusion 320, as by FIG. 12A.

Figure 13:
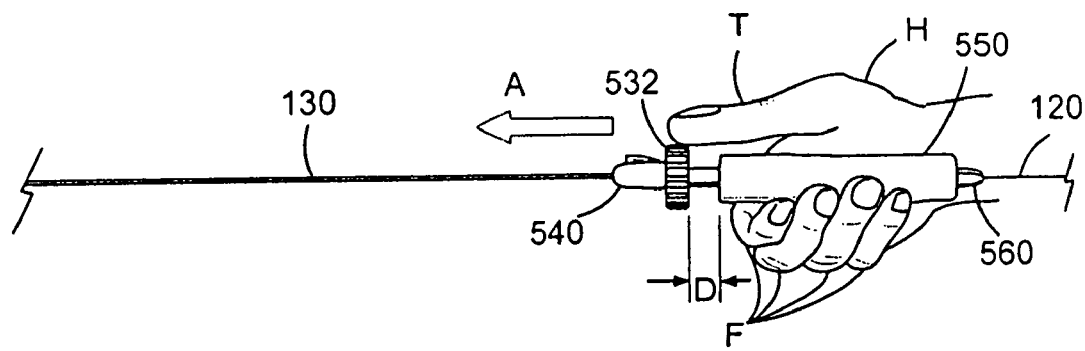
Figure 13:
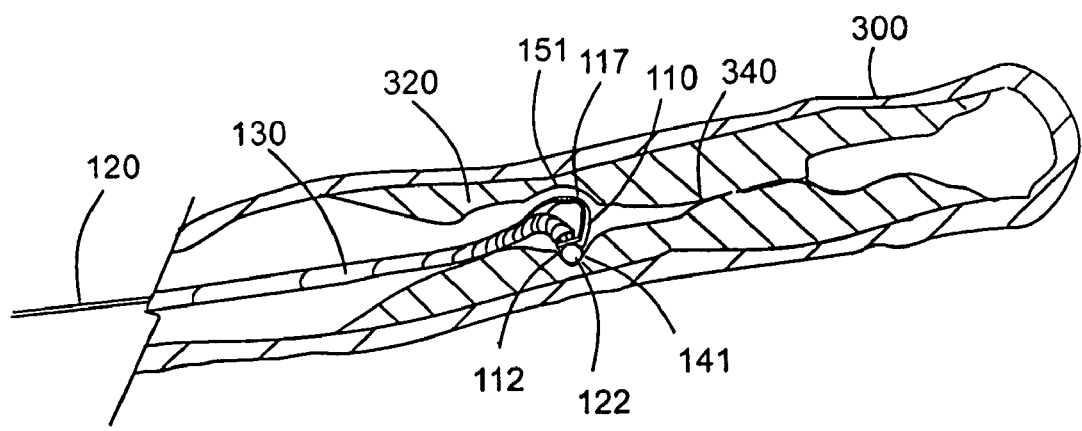

In a third step, as seen in ex vivo in FIG. 13A, with the force applicator 122 abutting on the face 112, and with both the shaft and the wire locking mechanisms, respectively 540 and 560 being locked, the collar 532 is pushed distally away from the wire handle 550, which is firmly retained, in the palm of the hand H by the fingers F of an operator OP. The collar 532 is pushed with the thumb T to translate distally, in a direction indicated by the arrow A, causing the shaft 130 to translate distally relative to the wire 120, through an axial distance D, for example, of 0.5 centimeters.

Transition from the expanded state following the arcuate state causes the tool tip MT to translate into the furrow 340 distally away from the arc depression, by one step length for each one sequence of operation. In the same manner, each next sequence of operation of the auger tool is accompanied by a next distal tip depression, and a next distal arc depression, and both the next distal tip and the next arc depression are disposed distally relative to, respectively, a previous tip and a previous arc depression. When the auger tool 100 is operated in a specific number of successive sequences, a same specific number of radial outward dilations and of distal translations accompanies these sequences.

Since the wire 120 remains locked in place while the shaft 130 is forced to translate distally, and the force applicator 122 remains in abutment against face 112, the resilient bow 110 is compelled to arcuate radially outward and away with respect to the guide wire 120, as shown in FIG. 13B. It is remarked that, as shown in FIG. 3, the face 112 is bent in oblique relative to the bow back 117, whereby the force applicator 122 first contacts the face 112 at a well predetermined point P, shown in FIG. 3, where initial bending moments are applied. Furthermore, relief 114 defines the location where the bow 110 will begin to flex, and arcuate.

As described hereinabove, the dimensions and the tapering of the flexible bow 110 are selected to ensure controlled predetermined curvature shapes for the radially outward bending of the bow 110 into a readily predictable mode of accurately defined deflection curvatures.

Referring to FIG. 13B and in other words, the force applicator 122 embeds into one portion of the occlusion 320, creating a first tip depression 141, into which the force applicator 122 anchors. With the force applicator 122 anchored into the first tip depression 141, the extrados of the flexed bow back 117 of the arcuate bow 110 engages and embeds into a diametrically opposite lateral portion of the occlusion 320, creating a first arc depression 151. The vessel 300 is thereby dilated asymmetrically and radially outward, and the furrow 340 will crack open, in a type of crack propagation process, successively opening distally into newly opened furrow portions. In fact, the bending bow 110 applies forces to expand the occlusion material and open a passage along a true lumen, which is the last blood flow path that was available before occlusion occurred.

It may thus be said that the tool tip MT of the auger tool 110 and the extrados of the bow back 117 are embedded and releasably retained in, respectively, the tip depression 141 and the arc depression 151 that are disposed opposite to each other in spaced-apart relationship in the vessel 300. Thereby the vessel is dilated asymmetrically in radial outward direction for opening a furrow 340 in the occlusion 320.

To further penetrate into the occlusion 320, the force applicator 122 has to progress distally to engage into and penetrate the newly opened furrow portion 340. To this end, as shown ex vivo in FIG. 14A, the collar 532 previously pushed through a distance D shown in FIG. 13A, is now gripped between the thumb T and the index IND. Then, the other fingers F are opened to release the grip of the palm of the hand H on the wire handle 550, as shown ex vivo in FIG. 14B. Thereby, the energy gathered in the arcuate bow 110 is released to push the face 112 distally, in the direction indicated by the arrow AR, until the wire handle 550 abuts on the collar 532.

The release of the energy-loaded bow 110 from the arcuate state to the extended state drives the face 112, and also the force applicator 122, distally into the furrow 340. When the flexed bow 110 is released, the first arc depression 151, into which the arcuate extrados of the bow back 117 is embedded, becomes a point of support wherefrom the face 112 uncoils distally. Therefore, with the first arc depression as support, the shape of the curvature of the flexed bow 110 is different from that of any shape developed during the bending of the bow 110.

While the distal portion of the bow 110, extending between the first arc depression 151 and the tip depression 141 is released to straighten out, the proximal support of the extrados gradually regresses proximally until return to the relief 114, which is reached in the expanded second state. This permits the force applicator 122 of the guide wire 120 to penetrate distally further into the furrow 340, as shown in vivo in FIG. 14C.

As stated hereinabove, the distal portion of the wire 120 that retains the force applicator 122, and the bow 110 that is disposed on the distal portion of the shaft 130, form the auger tool 100. The auger tool 100 is tensioned when the bow 110 is flexed to arcuate, by closing the distance separating the distal extremity of the shaft 130 from the face 112. When the bow 110 is released to expand and straighten out, the force applicator 122 is pushed distally further into the furrow 340.

Usually, a single two-step sequence of operation of the auger tool 100 is not sufficient to traverse and occlusion 320, and the sequence of coiling and uncoiling in worm-like crawling process must be repeated.

Figure 15:
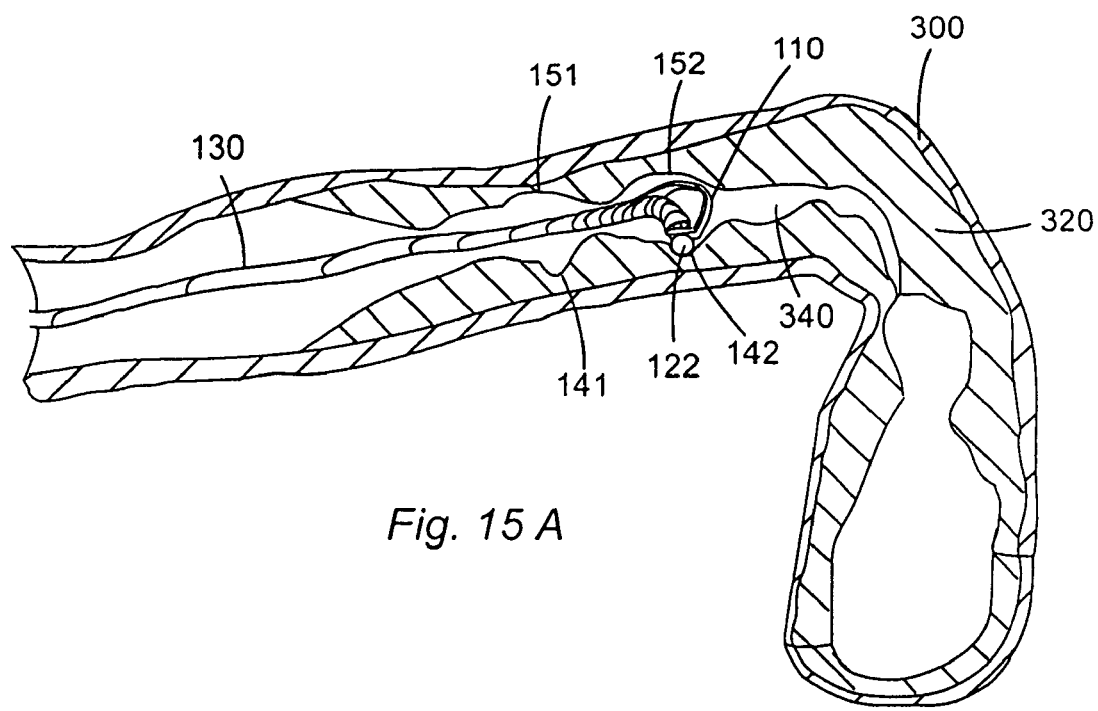
Figure 15:
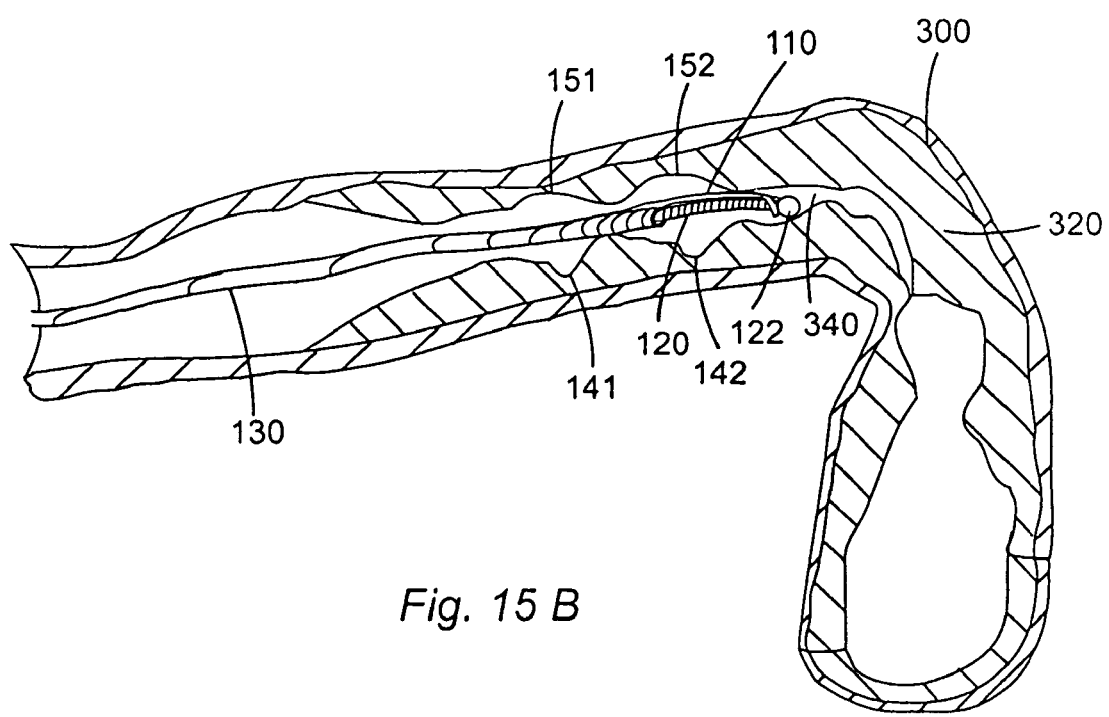

Once again, the collar 532 is pushed with the thumb T to translate distally, in the same manner as describe in relation to FIGS. 12B and 13A. In the bending phase of the crawling process, the bow 110 is arcuate, as shown in vivo in FIG. 15A, for the force applicator 122 to become engaged and anchored into a second tip depression 142, disposed distally away from the first tip depression 141. Likewise, the bow back 117 becomes engaged and anchored into a second arc depression 152, disposed distally away from the first arc depression 151, in a lateral portion of the occlusion 320, diametrically opposite to the second tip depression 142.

Figure 14:
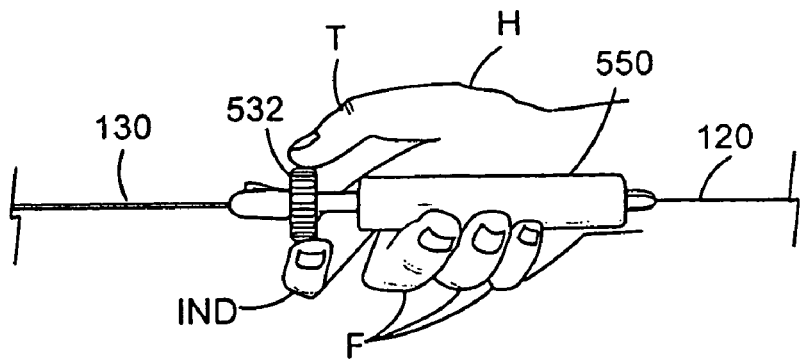
Figure 14:
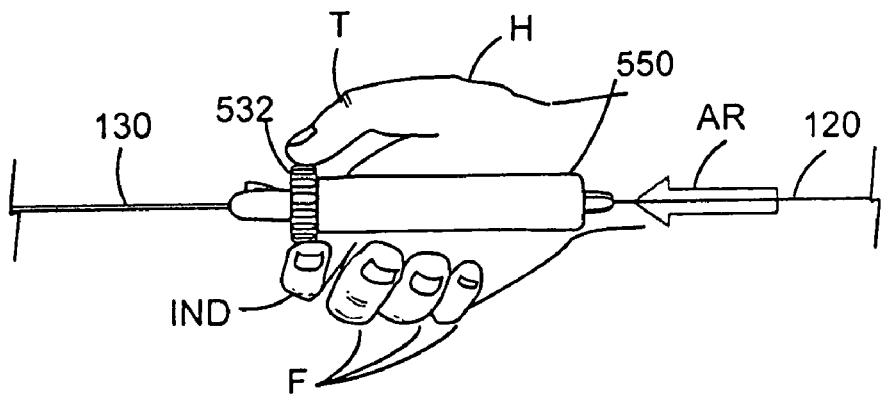
Figure 14:
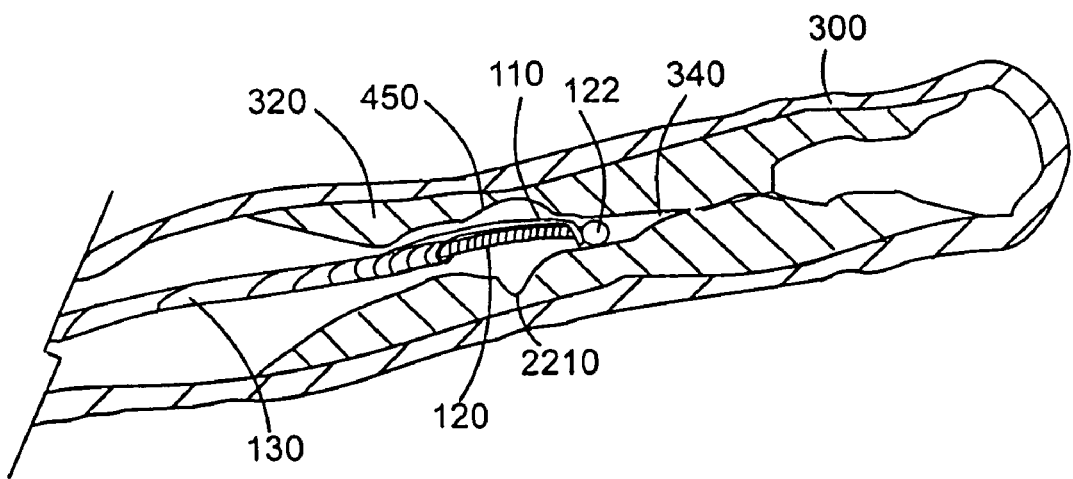

Finally, the collar 532 is gripped by the thumb T and the index IND, while the fingers F are released, in the same manner as described hereinabove in relation to FIGS. 14A and 14B. Thereby, the bow 110 expands and straightens out, distally past the second tip depression 142, and the bulb 122 is pushed to penetrate distally into the furrow 340, in the second step of the crawling process, as shown in vivo in FIG. 15B.

Once more, the force applicator 122 engages a newly formed crack opened by asymmetric radial dilatation of the vessel 300. The crawling process of the auger tool 100, as described hereinabove, may be repeated as often as needed to further penetrate into the occlusion 320, and finally, to traverse and exit distally out of that occlusion.

It is not necessary to describe in details that the auger tool 100 may be operated to traverse through a succession of occlusions disposed in the vessel 300, until the guide wire traverses and emerges distally away of the successive last occlusion. Typically, the bulb 122 progresses distally in successive steps of some 5 millimeters, prior to creating further tip and arc depressions.

During tests of the occlusion auger 1000, a flow passage through a 7-centimeter long occlusion 320, has been opened following 14 sequences of arcuate bending and expansion of the bow 110. In this manner, the occlusion auger 1000 may traverse a partial or a complete occlusion 320 of virtually any length, including a hard Chronic Total Occlusion.

It is remarked that the two-step sequence of flexing and expanding of the bow 110 is governed and controlled by the ex vivo auger actuator 500. This means that once the operator OP has selected and set values for a step-length, a shaft retention force limit, and a wire retention force limit, these selected values are maintained and will be repeatedly and identically applied in further successive sequences of operation, and will not rely on the skill and dexterity of the operator OP. For example, the operator OP may select and set the step-length distance D out of a range of say 1 mm to 20 mm, and the selected distance D is maintained throughout the consecutive sequences of operation performed by the auger tool 100, until set anew by the operator OP.

To help the operator OP using the occlusion auger 1000 to navigate and orient the force applicator 112 distally away, a radio-opaque dye 160 may be injected into the vessel 300. The interior of the vessel 300 thereby appears as a dark black area on the screen of an imaging system, clearly delimiting the borders of the vessel 300 and any occlusion 320. Thereby, tip depressions, lateral arc depressions, and cracks in a furrow 340 are well delimited. To further enhance the image presented to the practitioner, an image of the auger tool 100 taken prior to the injection of the dye 160 may be superimposed in contrast to the black dyed image, to define the disposition of the auger tool 100 relative to the occlusion 320.

Figure 16:
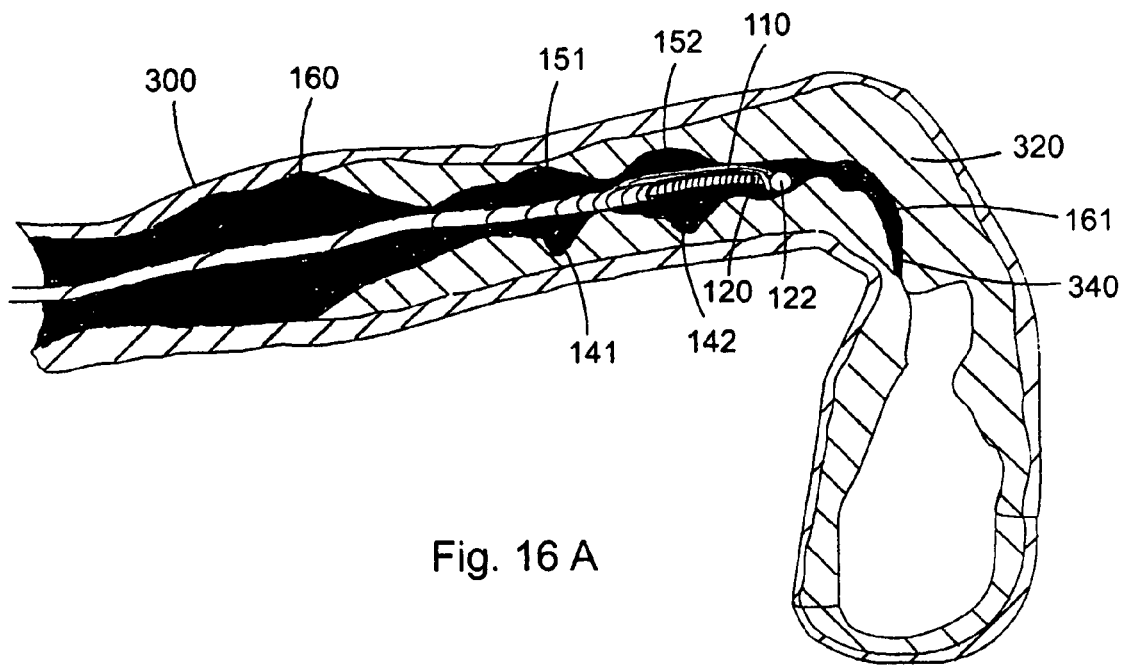
Figure 16:
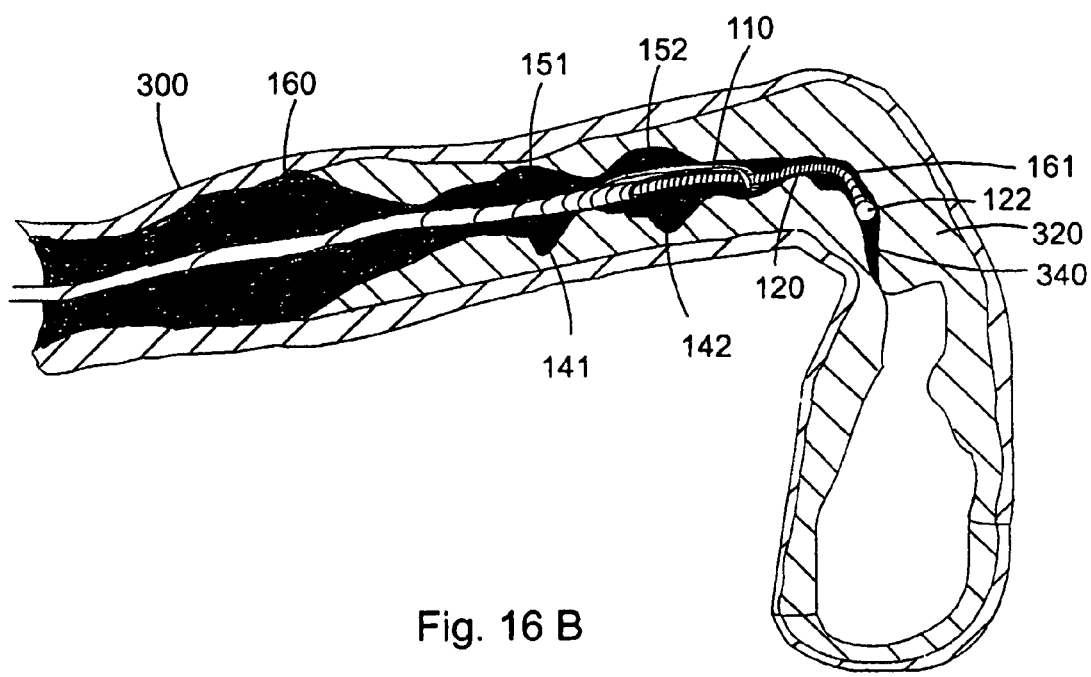

FIG. 16A illustrates an example of the use of radio-opaque dye 160 prior to taking a bend 161 in an occlusion 320. As delimited by the dye 160, the detected furrow 340 offers a narrow bent lumen extending distally away ahead of the bulb 122. The operator will respond to such a vessel configuration by trying to navigate the wire 120 accordingly, and insert the force applicator 122 as distally away as possible.

To this end, the wire locking mechanism 560 is released while the shaft-locking mechanism 540 remains locked, and the wire 120 is manually translated distally, and rotated if necessary, until the wire 120 penetrates the furrow 340 as distally as possible, as shown in vivo in FIG. 16B. The accompanying manipulation of the auger control assembly 500 was described hereinabove, and is not repeated.

Figure 17:
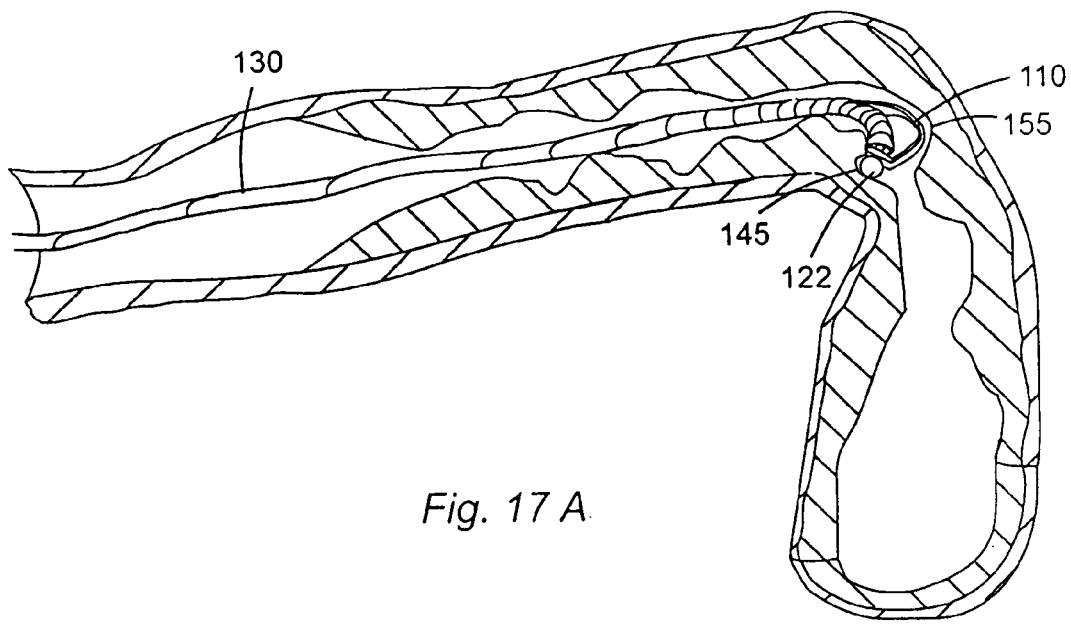
Figure 17:
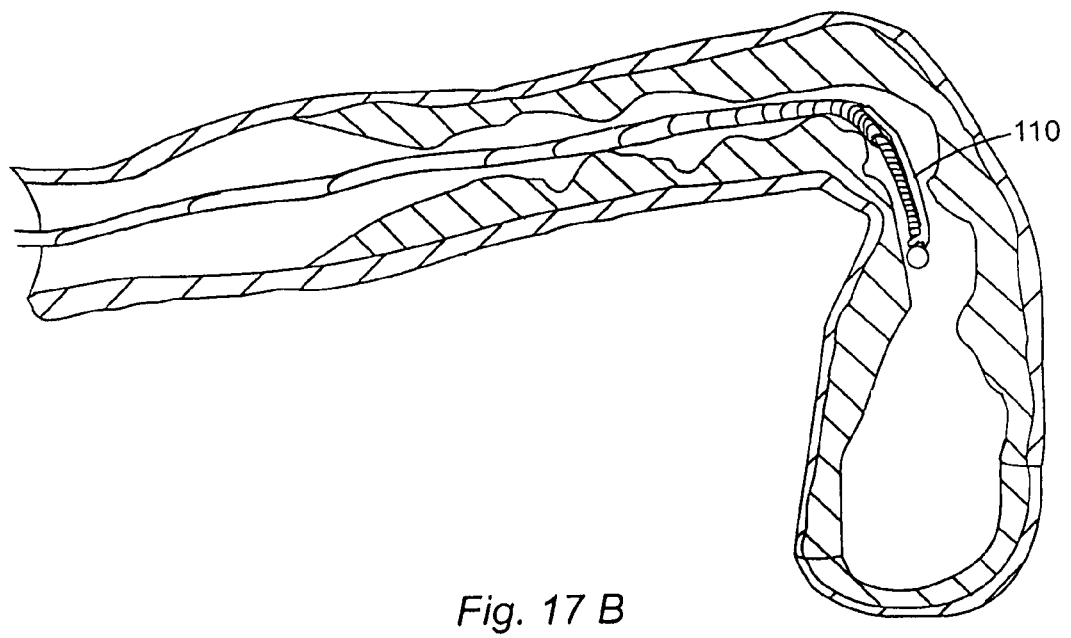

To traverse through a further distally disposed occlusion 320, the auger tool 100 has to be operated again in a sequence of two-phased crawling process steps. FIG. 17A depicts in vivo the arcuate bending of the bow 110, creating the asymmetric radial dilatation, and FIG. 17B presents the longitudinal straightening out and expanded bow 110, where the force applicator 122 is shown distally away through and past the occlusion 320. The auger tool 100 has thus embedded one more tip depression 145 and one more arc depression 155. Further successive crawling steps, in addition to the single step described hereinabove may be required to pierce past a more massive and longer occlusion 320.

Figure 18:
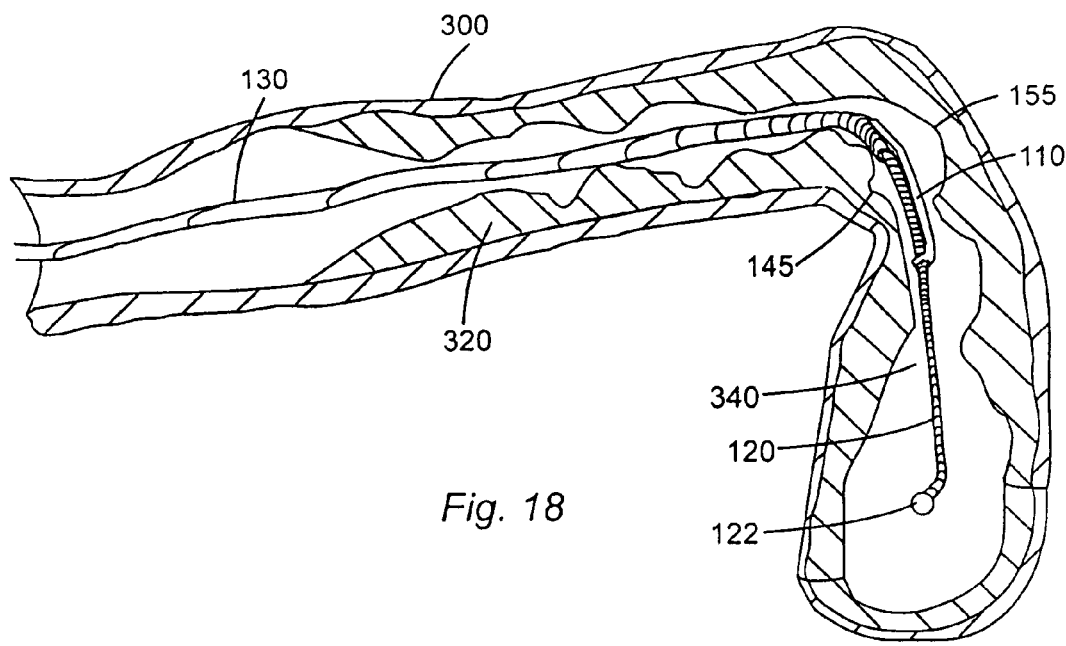

The occlusion auger 1000 may serve as a guide for additional surgical instruments used in simultaneous and/or following procedures. For example, the wire 120 may be disposed distally away from the occlusion 320, as shown in FIG. 18, whereafter the shaft 130 is retrieved proximally away, for the wire 120 to serve as a guide to an angioplasty catheter supporting, as desired, a balloon with or without a stent.

To dispose the force applicator 122 and the wire 120 distally outward and away from the occlusion 320, the wire-locking mechanism 560 is unlocked while the shaft-locking mechanism 540 remains locked. Then, the guide wire 120 if pushed distally into the interior of the vessel 300, well distally past the occlusion 320, a shown in vivo in FIG. 18.

Then, the auger tool 100 is retrieved ex vivo in proximal translation over the shaft 130. For this purpose, the proximal portion of the guide wire 120 is held stationary in one hand, while the other hand retrieves the auger actuator 500, and therewith also the shaft 130, by proximal translation of the face bore 113 over the shaft 130. This is achieved after the wire-locking mechanism 560 is unlocked and the shaft-locking mechanism 540 is locked.

In an alternative procedure to distally remove the shaft 130 ex vivo, the operator may choose to unlock both the shaft-locking mechanism 540 and the wire-locking mechanism 560, and then remove the auger actuator 500 in proximal translation over the shaft 130 and the wire 120, after which, the shaft 130 is translated proximally with respect to the wire 120, which remains in place.

Enhancements

Figure 19:
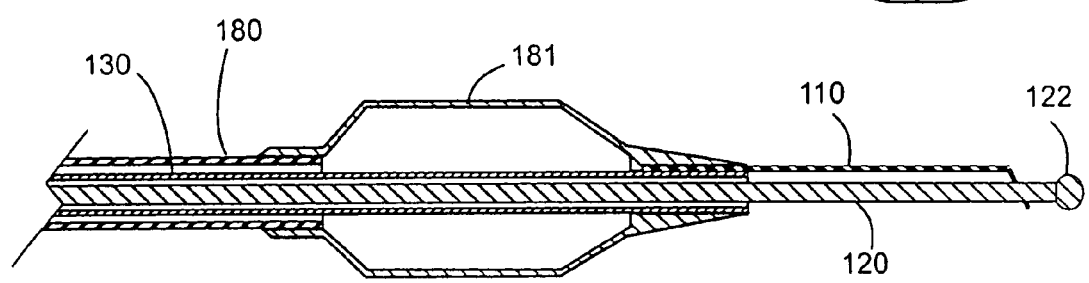
FIGS. 19A and 19B shows enhancements of the occlusion auger of FIG. 1, FIGS. 20A to 20D illustrate the mechanism of bending and expansion of the occlusion auger of FIG. 1, FIGS. 21A to 21C depict various bow root configurations.
Figure 19:
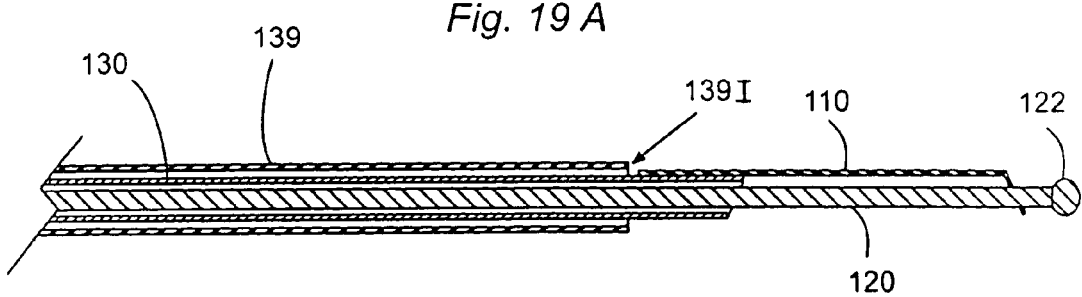

During operation of the occlusion auger 1000, it is possible to prevent proximal blood flow by use of an angioplasty catheter 180 with a balloon 181, disposed around the shaft 130, as shown in FIG. 19A. If desired, the inflation of the balloon may be applied to symmetrically dilate the vessel 300 and to enhance the opening of a distal crack in the furrow 340. Optionally, the angioplasty catheter 180 supports a stent, for use after operation.

Since it is possible to insert additional treatment tools in vivo over the shaft 130 and over the auger tool 100, it becomes superfluous to proximally retrieve the shaft 130 ex vivo after completion of the procedure using the occlusion auger 1000. Therefore, after use of the occlusion auger 1000, the auger tool is left in place in vivo, and an additional treatment tool is translated in vivo, over the auger tool, and disposed for further in vivo treatment.

In case of an acute occlusion, the bow 110 may be flexed to a selected degree, and be rotated about the wire 120 to cut into and disintegrate the thrombotic material of the occlusion. However, when operating the occlusion auger 1000, it is possible that in the case of myocardial infraction, or MI, deriving from total occlusion, embolic particles may be released into the distal arterial structure. To prevent such an incident, it is desirable to provide for aspiration of these emboli. Aspiration is possibly achieved via the shaft 130, or by any other duct or lumen allowing fluid communication from an aspiration opening of the duct disposed in vivo at or proximate the distal extremity of the occlusion auger 1000, and leading to an exhaust exit opening of the duct, disposed ex vivo.

FIG. 19B illustrates a suction duct 139 with a suction intake 139I opening adjacent the distal portion of the auger tool 100, appropriately configured and disposed to discharge any dislocated occlusion debris to an exhaust opening, not shown in FIG. 19B, but disposed ex vivo.

Mechanism of Bending and Expansion

Although described hereinabove, the mechanism governing the two-step sequence of operation of the auger tool 100, with the bow 110 bending and expansion process, is now schematically described in further detail, since the successive shapes of bow curvature during the expansion state are not identical, in reverse, to the successive shapes of bow curvature during the bow 110 flexing state.

Figure 20:
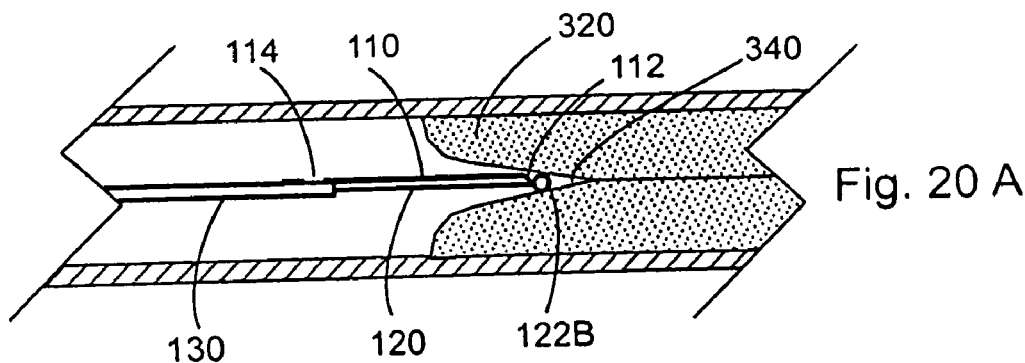
Figure 20:
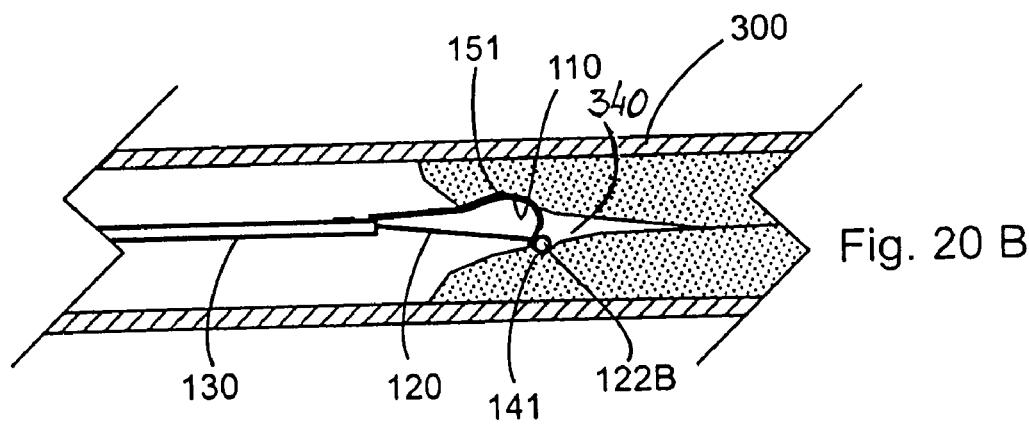
Figure 20:
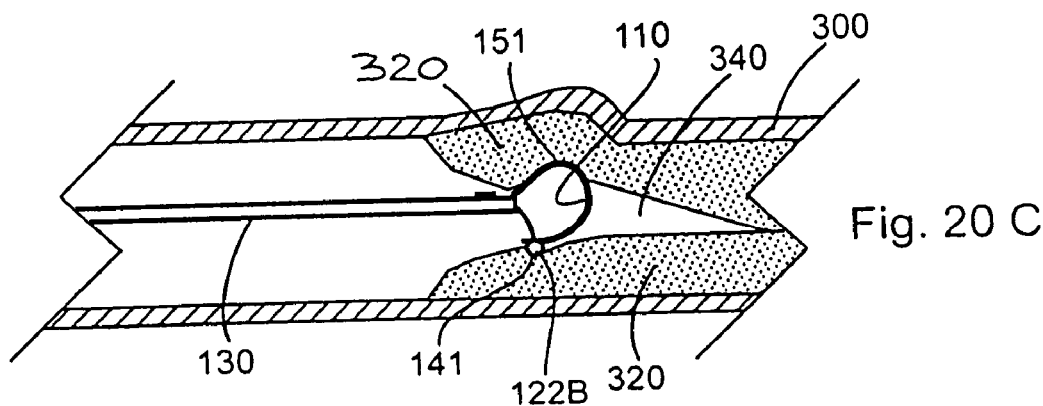
Figure 20:
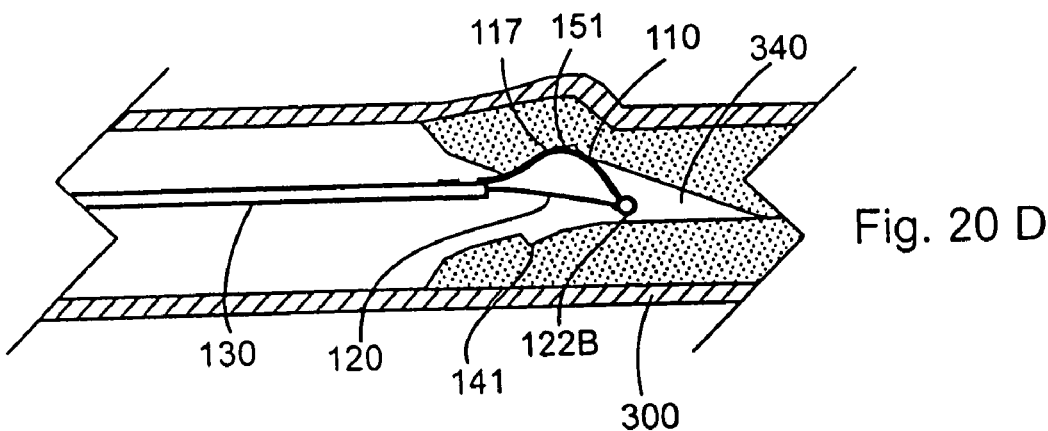

In a preferred embodiment 1000, illustrated schematically in FIG. 20A, when in the expanded state, the bow 110 is analog to a flat spring cantilevered to the shaft 130 at the relief 114 and having the face 112 as a free end. To flex the bow 110 into the arcuate state, the shaft 130 is distally translated toward the force applicator 122B, which is retained in place by the locked wire 120, disposed against the occlusion 320, as by FIG. 20B.

It was described hereinabove that the bow 110 is configured to taper and that the bow back 117 present a distally diminishing rigidity, thus a decreasing spring rate or spring coefficient, smallest adjacent the face 112. Therefore, when the bow is loaded to flex, the "softer" distal extremity bends first, followed by proximal portions of the bow back 117, coiling the bow back 117 to gradually roll in atraumatic deflection into occlusion tissue.

In FIG. 20B, force is applied on the face 112, shown in FIG. 20A, and the bow starts to arcuate under the applied bending moment, in gentle and gradual atraumatic rolling motion, into occlusion tissue of the furrow 340. Simultaneously, the bulb 122B embeds into a tip depression 141 and the extrados of the bow 110 embeds in an arc depression 151.

In a further bow curvature deflection phase depicted in FIG. 20C, the bow 110 has further coiled-up and rolled into the occlusion 320, anchoring the extrados deeper into the occlusion tissue, deepening the arc depression 151, and asymmetrically dilating the vessel 300 radially outward. The bow flexing process ends when the face 112 practically abuts the distal extremity of the shaft 130.

When flexed to arcuate as shown in FIG. 20C, the arc depression 151 extends distally relative to the tip depression 141. However, the arc depression may have a span selected from the group of spans consisting of a span extending proximally and distally relative to the tip depression, a span extending proximally relative to the tip depression, and a span extending distally relative to the tip depression.

The bow 110 is thus appropriately configured with a distally gradually diminishing spring rate coefficient for deflection under larger force at the bow root and under smaller force at the face, whereby controlled atraumatic bow deflection curvature is achieved. Therefore, the arc depression of the extrados is larger and more pronounced than the tip depression.

In return to the expanded state, and in reference to FIG. 20D, the shaft 130 is retained in place while the wire 120 is gradually released distally, relieving the bending moment applied to the bow 110. The extrados of the bow back 117, which remains embedded in the deepened arc depression 151, becomes a point of support wherefrom the face 112 uncoils distally. The bow 110 now presents an active distal portion spanning from the arc depression 151 to the tip depression 141, in contrast with the flexing state where the span ranged from the relief 114 to the tip depression 141. Therefore, the shape of the curvature of the expanding bow 110 is different from that of any shape developed during bending.

The distal portion of the bow back 117 thus gradually uncoils in gentle atraumatic motion to push the force applicator 122 distally into the newly opened and deepened furrow 340. While the distal portion of the bow 110, extending between the first arc depression 151 and the tip depression 141 is released to straighten out, the proximal support of the bow 110 gradually regresses proximally toward the relief 114, which is reached upon return to the fully expanded state. This permits the force applicator 122 of the wire 120 to penetrate distally further into the furrow 340, as shown in vivo in FIG. 14C.

In addition, the controlled force threshold, step length limit and deflection curve of the bow 110 provide for control of the radial dilation and forces applied to the occlusion and to the vessel 300.

The mechanism by which the auger tool operates is configured for flexing the bow back 117 into well controlled deflection curve shapes, and for embedding the tool tip MT first, and thereafter the extrados, to induce atraumatic rolling motion necessary for the radial outward dilation, and for the distal translation. In other words, the auger tool 100 translates substantially axially and distally into the vessel 300 in successive crawling motion imparted by each successive sequence of operation.

Finally, the mechanism of operation provides for an auger tool 100 void of free-extending traumatic extremities: The bow back 117 has an extrados extending radially outward and away from the wire 120, but the bow root 115 is retained to the shaft 130, and the face12 is retained to the wire 120 by the face bore 113, not only for continuous control of the deflection of the bow 110, but whereby there is provided for the force applicator 122 to be the sole free-extending extremity of the auger tool 100.

ALTERNATIVE EMBODIMENTS

Figure 21A:
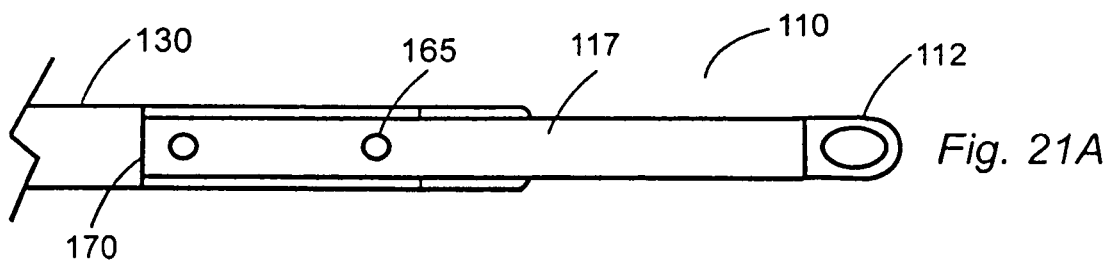
Figure 21B:
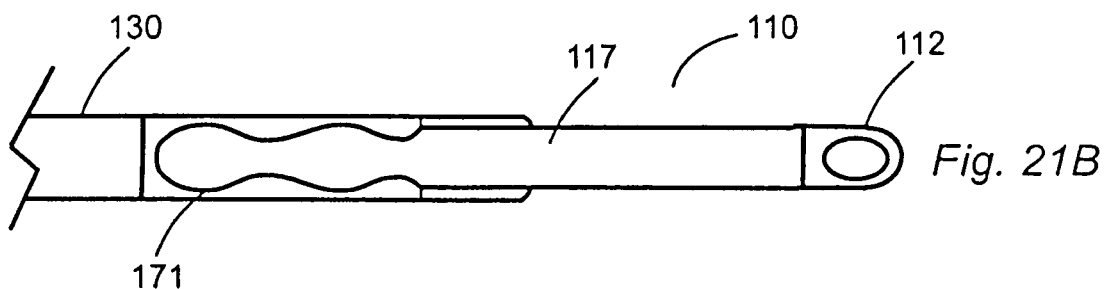
Figure 21C:
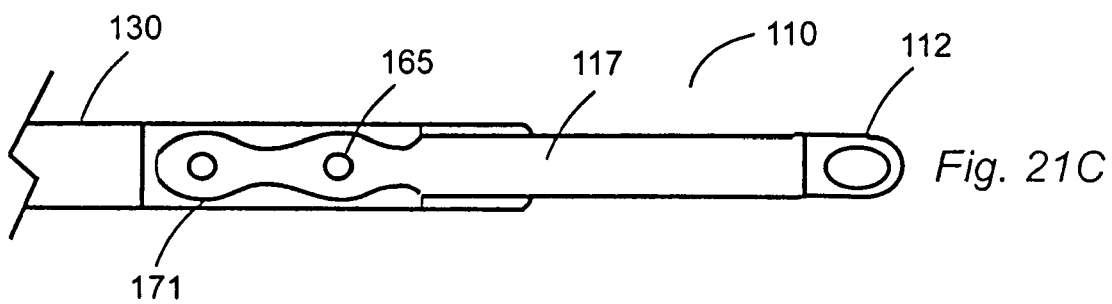

FIGS. 21A to 221C are top elevations of the bow 110 and of the distal extremity of the shaft 130, showing alternative embodiments of the configuration and of the method used for retention of the bow root 115 to the shaft 130. The bow root 115 is best shaped to fit the functional demands required by the manufacturing techniques applied for the retention of the bow 110 to the shaft 130. For example, for fastening the bow root 115 by means of rivets 165 to the shaft 130, as shown in FIG. 21A, a rectangular shape 170 for the bow root 115 is well suited, but an hourglass shape 171, shown in FIG. 21C, will suffice. However, the hourglass shape 171 shown in FIG. 21B for retention of the bow root 115 to the shaft 130, may provide a better grip for fastening by help of a shrink tube 116. Nevertheless, other configurations of the shape of the bow root 115 may be selected to better suit other fastening means for chemical or physical bonding, such as crimping, or any kind of soldering, brazing, welding, and diffusion fastening. In fact there is no limit to the choice of shapes for the bow root 115, and for the retention means of the bow root 115 to the shaft 130.

Figure 22A:
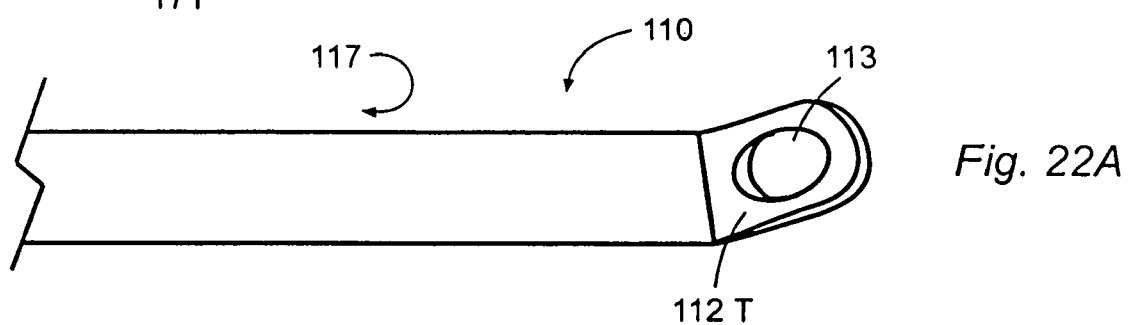
FIGS. 22A and 22B present optional embodiments of the face of the bow.
Figure 22B:
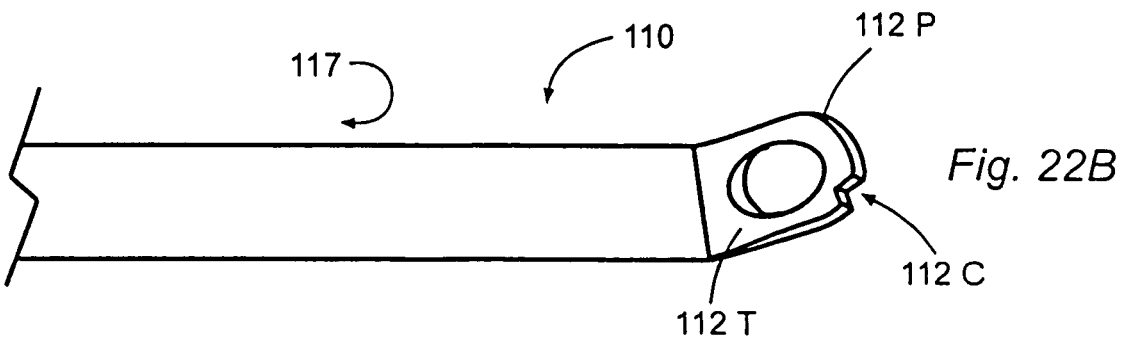

FIGS. 22A and 22B illustrate an alternative embodiment of the bow 110, shown in bottom elevation. Instead of having a planar face, or flat-plane face 112, as seen in FIGS. 2 and 3, the alternative embodiment has a twisted face 112T presenting a pitch angle. When the expanded and straightened-out bow 110 is rotated, the face 112T operates as a segment of a screwthread with a pitch angle to threadingly engage and progress through the occlusion 320.

To further enhance the abilities of the bow 110, with either a planar face 112, or a twisted face 112T, the perimeter 112P of the face may be configured as a cutting tool with a plurality of, but with at least one cutting-edge 112C, as shown in FIG. 22B. When rotated, the twisted face 112T may chip through the occlusion 320. It is noted that the type of face, either the planar face 112 or the twisted face 112T, does no affect the controlled bending properties of the bow 110.

As described hereinabove, the proximal retraction of the shaft 130 was achieved by sliding the face bore 113 of the bow 110, over the wire 120. This retraction method implies that the interior diameter of the face bore 113 must be large enough to permit the passage therethrough of the widest dimension of the wire 120. In a preferred embodiment, the force applicator 122 has a diameter wider than the interior diameter of the face bore 113. However, to penetrate thin vessels 300, it is advantageous to keep the dimensions of the bow 110, of the face 112, and of the force applicator 122, as small as possible.

To further reduce the dimensions of the auger tool 100, an alternative auger tool 200 is described hereinbelow, by which, when desired, the shaft 130 may become disengaged from the wire 120 and be retrieved proximally ex vivo, even though the interior diameter of the face bore 113 is smaller than the widest dimension of the shaft 130 and of the force applicator 122.

FIGS. 23A to 23C illustrate a distal portion of the auger tool, as embodiment 200, with a different type of force applicator 122 and face 112, and with reduced dimensions. In FIGS. 23A to 23C reference is made to the planar face 112, but the same applies to the twisted face 112T, with and without one or more cutting-edge(s) 112C.

As shown in FIG. 23A, the force applicator 122 is configured as a limited length of male screwthread 122M disposed at the distal extremity of the wire 120, instead of the bulb 122B shown in FIGS. 2 and 3. The face 112, shown in FIG. 23B, operates as a female screwthread 113F, or may be fitted therewith, in replacement of the cylindrical face bore 113, to receive the male screwthread 122M therein in matching and in extension therethrough.

To extend the male screwthread 122M distally outward of the face 112, as shown in FIG. 23C, the male screwthread 122M is rotated and threadingly engaged until distally emerging thereout. Thereafter, once disposed distally out and away of the face 112, the male screwthread 122M will operate as a force applicator 122 when the wire 120 urges the face 112. In distal translation of the shaft 130 relative to the static force applicator 122M, the male screwthread 122M will apply bending moment forces on the face 112 to arcuate the bow 110. It is noted that the face bore 113, or the female screwthread 113F, have a minimal inside diameter designated as w in FIG. 23B, whereas the same dimension w as shown on the male screwthread 122M in FIG. 23A, is smaller than the maximal external diameter of the force applicator 122.

The auger tool 200 having a distal male screwthread 122M, operates in the same manner as the auger tool 100 with the bulb 122B, to create a tip anchoring depression 141 when the bow is flexed to arcuate. However, in the embodiment 200, the male screwthread 122M has reduced dimensions when compared to the bulb 112B. For example, the male screwthread 122M has a maximal diameter ranging between 1.5 mm and 0.09 mm.

With the auger tool 200, when the operator desires to proximally retrieve the shaft 130 ex vivo, then the wire 120 is first rotated in screwthread unfastening rotation until the screwthread 122M is released proximally out of the face 112 or the face 112T, as shown when taking the FIGS. 23A and 23B in mutual relation. Next, the shaft is pulled proximally causing the bow 110 to slightly flex radially outward, to enable sliding over the male screwthread 122M and over the length of the wire 120, and its supporting coils.

Another embodiment 600 of the auger tool is described, requiring limited angular rotation of the wire 120 for release from the face indicated as face 112 but also including face 112T.

Reference is first made to the auger tool 100, to better emphasize differences. FIG. 24A shows a circular face bore 113, opened in the face 112, when the bow 110 is seen in front elevation. Corresponding thereto is the substantially spherical bulb 122B, also sown in front elevation, seen in FIG. 24B.

In the same manner, FIG. 25A depicts a face 112 with an oval face bore 113OV, and FIG. 25B shows a matching ovaloid force applicator 122OV.

It is readily understood that when the main axis of the ovaloid force applicator 122OV is appropriately aligned with the main axis of the oval face bore 113OV, then translation of the wire 120 into and through the face 112 is possible. However, when the main axes of the ovaloid 122OV and of the oval face bore 113OV are out of mutual alignment, say at right angle, as shown in FIG. 25C, then distal extension translation or proximal retrieval translation through the face 122 is prevented. The operator OP just has to rotate the wire 120 say by 90° relative to the face 112, to switch from retention of the wire 120 to the face 112, or release therefrom.

In brief, the force applicator 122 is permanently attached to the distal extremity of the wire 120, and the force applicator 122 and the face bore 113 are configured for either one of both, permitting passage of the force applicator through the face bore, and preventing passage of the force applicator through the face bore. Likewise, the force applicator 122 and the face bore 113 are configured for both, permitting passage of the force applicator 122 through the face bore 113, and preventing passage of the force applicator 122 through the face bore 113. Thus, the force applicator 122 is retained to the face 112 in proximally controlled attachment release.

If desired, a minute portion 122T of the wire 120 may extend distally outward of the force applicator, shown as bulb 122B in FIG. 26, but applicable to any force applicator 122. The tip portion 122T helps to better anchor the force applicator 122 into a tip depression 141 created in occlusion tissue.

It will be appreciated by persons skilled in the art, that the present invention is not limited to what has been particularly shown and described hereinabove. For example, the auger tool may have other configurations, as long as atraumatic rolling motion is provided. Furthermore, the auger tool 100, which has at least one flexible portion, may have more such portions. Likewise, the auger tool 100 my have one or more resilient portion(s). Moreover, the auger control for automatic repetition of the sequences of operation. Rather, the scope of the present invention is defined by the appended claims and includes both combinations and sub-combinations of the various features described hereinabove as well as variations and modifications thereof which would occur to persons skilled in the art upon reading the foregoing description.

The invention claimed is:

1. A method for distally traversing an occlusion in a vessel having vessel walls, the method comprising:
   providing an occlusion auger including a shaft;
   providing an auger tool including a flexible and resilient beam having a proximal end and a distal free end, the distal free end of the beam forming a face, the proximal end of the beam being fixed to the shaft such that the beam forms a cantilevered bow having a bow back configured as a flat spring, and the bow back having a distal taper that provides a lower spring rate at the distal free end of the beam than at the proximal end of the beam;
   configuring the auger tool for atraumatic repeatable operation in a sequence including both deflection of the auger tool to an arcuate state in which it extends radially outward, and release of the auger tool from the arcuate state to an expanded and straight state, and vice versa, the auger tool having an extrados when arcuate, and a tool tip;
   disposing the auger tool so as to be adjacent to the occlusion; and then
   moving the auger tool into the arcuate state with the tool tip and the extrados being embedded and releasably retained in, respectively, a tip depression and an arc depression disposed opposite to each other in a spaced-apart relationship in the vessel such that the vessel is dilated asymmetrically in a radial outward direction for opening a furrow in the occlusion.

2. The method according to claim 1, further comprising, after moving the auger tool into the arcuate state, releasing the auger tool from the arcuate state so as to cause the auger tool to move into the expanded state wherein the tool tip and the extrados are released from, respectively, the tip depression and the arc depression; and the tool tip translates into the furrow distally away from the arc depression, by one step length for each one sequence of operation.

3. The method according to claim 2, wherein:

each next sequence of operation of the auger tool is accompanied by a next distal tip depression and a next distal arc depression, and both the next distal tip and the next arc depression are disposed distally relative to, respectively, a previous tip and a previous arc depression.

4. The method according to claim 3, wherein:

the auger tool is configured for flexing in a controlled deflection curve shape, and embedding the tool tip first, and thereafter the extrados induces atraumatic rolling motion for (i) radial outward dilation, and (ii) distal translation.

5. The method according to claim 4, wherein:

the auger tool is configured such that elastic energy accumulated by the bow while flexing when the auger tool is moved into the arcuate state is liberated to expand the bow when the auger tool is released into the expanded state, and operation of the auger tool in a specific number of successive sequences is accompanied by a same specific number of radial outward dilations and of distal translations.

6. The method according to claim 5, wherein:

the auger tool translates substantially axially and distally into the vessel in successive crawling motion imparted by each successive sequence of operation, each next sequence of operation of the auger tool is accompanied by a next distal tip depression and a next distal arc depression, and both the next distal dip depression and the next arc depression are disposed distally relative to, respectively, a previous tip depression and a previous arc depression.

7. The method according to claim 1, wherein:

the shaft has an ex vivo proximal end, an in vivo distal end, an exterior, and an interior supporting therein a wire having an ex vivo proximal extremity portion and an in vivo distal extremity portion, the bow of the auger tool is disposed in distal coextensive longitudinal alignment with the distal end of the shaft, the bow back of the bow is intermediate a bow root fixedly attached to and supported by the distal end of the shaft, the face formed at the distal free end of the bow extends distally away from the bow back, the face having a face bore which is configured for passage therethrough of the wire, and a force applicator retained at the distal extremity of the wire and configured for operative association with the face bore and with the shaft, to (i) flex the bow to the arcuate state when the shaft is translated distally relative to the force applicator, for the extrados to dilate the vessel asymmetrically in the radial outward direction, and (ii) release the bow to the expanded state when the wire is released, for the face to translate the force applicator distally away relative to the arc depression by one predetermined step length for each one sequence of operation.

8. The method according to claim 7, wherein:
the bow has at least one flexible element.

9. The method according to claim 7, wherein:
the bow has at least one resilient element.

10. The method according to claim 7, wherein:
the force applicator is disposed in longitudinal coextensive distal alignment with the face, and
the bow is tangential to and longitudinally aligned with the shaft, and is configured to taper from the bow root distally away to reduce dimensions, thereby forming a single protrusion extending radially outward relative to the wire, whereby alignment of the force applicator with the face, tapering of the bow, and the single radial protrusion enhance reduced dimensions.

11. The method according to claim 7, wherein:
the force applicator is permanently attached to the distal extremity of the wire, and
the force applicator and the face bore are configured for one of (i) permitting passage of the force applicator through the face bore, and (ii) preventing passage of the force applicator through the face bore.

12. The method according to claim 7, wherein:
the force applicator and the face bore are configured for both permitting passage of the force applicator through the face bore, and preventing passage of the force applicator through the face bore.

13. The method according to claim 7, wherein:
the force applicator is retained to the face in a proximally controlled attachment release.

14. The method according to claim 7, wherein:
the bow is tapered to reduce dimensions;
the bow is configured with a distally gradually diminishing spring rate coefficient for deflection under larger force at the bow root and under less force at the face, and
the arc depression of the extrados is larger than the tip depression.

15. The method according to claim 7, wherein:
an auger control is disposed ex vivo in operative association with the auger tool, the auger control comprising:

a common axial conduit configured to accommodate bi-directional translation therethrough and bi-directional rotation of the wire, the wire being retrievable distally and proximally, wherein a distal portion of the conduit is configured to accommodate bi-directional displacement in translation and in rotation of the shaft, the shaft being retrievable distally;

two force limiters, including a wire force limiter operatively coupled to the wire and a shaft force limiter operatively coupled to the shaft, configured for adjustable selection and setting of a predetermined threshold limit of forces applied to the auger tool; and a step limiter configured for adjustable selection and setting of a predetermined distal step length taken in each one sequence of operation, wherein the wire, the shaft and the two force limiters are operative independently and in combination.

16. The method according to claim 15, wherein:
the auger control maintains identical predetermined forces limit and step length settings for each sequence in a series of successively repeated sequences.

17. The method according to claim 15, wherein the auger control further comprises:
a shaft lock for releasably locking the shaft relative to the auger control and for limiting force applied on the shaft;

a stepper for distally translating the shaft in predetermined step length; and a wire lock for releasably locking the wire relative to the auger control and for limiting force applied on the wire; and wherein the auger control is configured for operative handling and control of the wire and of the shaft both independently and in combination.

18. The method according to claim 7, wherein, in the arcuate state of the auger tool:

the bow back has the extrados and the extrados extends radially outward and away from the wire, and the bow root is retained to the shaft and the face is twisted to present a pitch angle and is retained to the wire by the face bore, for continuous control of the deflection of the bow, whereby the force applicator is the sole free-extending extremity of the auger tool.

19. The method according to claim 7, wherein:

at least one cutting edge is disposed on a perimeter of the face to extend radially outward and away from the face bore, and the at least one cutting edge is configured for radially cutting into occlusion tissue, by operating in vivo as a segment of a screwthread with a pitch angle to threadingly engage and progress through the occlusion.

20. The method according to claim 7, wherein:

(a) the force applicator is navigated to engage an axial furrow in an occlusion, (b) the face is abutted on the force applicator, (c) the auger tool is operated to the arcuate state of the bow to gather energy, whereby kinetic energy is accumulated and the bow asymmetrically dilates the vessel into one radial outward direction, (d) the energy gathered in the arcuate bow of the auger tool is released to the expanded state, and the released kinetic energy extends the bow to translate the force applicator distally into the furrow, and (e) the sequence of steps (c) and (d) are successively repeated until augmented blood flow is restored.

21. The method according to claim 7, wherein, in the arcuate state of the auger tool:

the force applicator releasably embeds in a tip depression, and the extrados embeds in an arc depression to dilate the furrow, and to initiate a crack propagation mechanism to open and distally deepen the furrow, and wherein, in the expanded state of the auger tool:

the force applicator is received by one step length distally deeper in the deepened furrow.

22. The method according to claim 17, wherein when the force applicator extends distally past an occlusion, one of (i) the wire is navigated to engage a next occlusion and a next occlusion traversing sequence is performed, and (ii) the shaft is proximally retrieved ex vivo while the wire remains disposed in place for use in a next treatment intervention.

23. The method according to claim 17, wherein when the force applicator extends distally past a traversed occlusion, the shaft is retrievable ex vivo, by one of (i) retrieving the face bore proximally away relative to the force applicator and sliding the face bore over the wire, and (ii) disengaging the face distally away from the force applicator, and retrieving the shaft proximally.

24. The method according to claim 7, wherein:

the step length ranges from 1 mm to 50 mm.

25. The method according to claim 7, wherein:

the tip depression is disposed opposite the arc depression, and the arc depression has a span selected from a group of spans consisting of a span extending proximally and distally relative to the tip depression, a span extending proximally relative to the tip depression, and a span extending distally relative to the tip depression.

26. The method according to claim 1, further comprising fixing the proximal end of the beam to the shaft such that a portion of the beam extends alongside the shaft.

27. The method according to claim 1, further comprising fixing the proximal end of the beam to the shaft such that relative motion between the beam and the shaft is prevented.

28. The method according to claim 1, further comprising passing a wire through the shaft and through a face bore in the face at the distal free end of the beam, the beam being fixed to the shaft such that a portion of the beam extends alongside a portion of the shaft through which the wire passes.

* * * * *